United States Patent [19]

Szczepanski et al.

[11] Patent Number: 4,898,607
[45] Date of Patent: Feb. 6, 1990

[54] HERBICIDAL IMIDAZOLE DERIVATIVES

[75] Inventors: Henry Szczepanski, Wallbach, Switzerland; Lourens Wals, Turnhout, Belgium

[73] Assignee: Ciba-Geigy Corporation, Ardsley, N.Y.

[21] Appl. No.: 234,240

[22] Filed: Aug. 18, 1988

[30] Foreign Application Priority Data

Aug. 25, 1987 [CH] Switzerland ............... 3242/87

[51] Int. Cl.$^4$ .................. A01N 43/50; C07D 233/90
[52] U.S. Cl. .......................................... 71/92; 540/543; 540/603; 546/15; 546/203; 546/204; 546/205; 546/206; 548/336; 548/343
[58] Field of Search .............. 548/343, 336; 546/15, 546/203, 204, 205, 206; 540/543, 603; 71/92

[56] References Cited

FOREIGN PATENT DOCUMENTS

| 207563 | 1/1987 | |
| 2345656 | 9/1987 | European Pat. Off. |
| 240050 | 10/1987 | European Pat. Off. |
| 273531 | 7/1988 | European Pat. Off. |
| 275603 | 7/1988 | European Pat. Off. |
| 277384 | 8/1988 | European Pat. Off. |
| 277387 | 8/1988 | European Pat. Off. |
| 287512 | 10/1988 | European Pat. Off. |
| 289066 | 11/1988 | European Pat. Off. |

OTHER PUBLICATIONS

*Chem. Abstracts*—vol. 67 (1967) 115596z.
*Chem. Abstracts*—vol. 68 (1968) 95758u.
*Chem. Abstracts*—vol. 69 (1968) 19160y.

*Primary Examiner*—Richard A. Schwartz
*Attorney, Agent, or Firm*—Kevin T. Mansfield; Edward McC. Roberts

[57] ABSTRACT

1,5-substituted imidazole derivatives of formula I

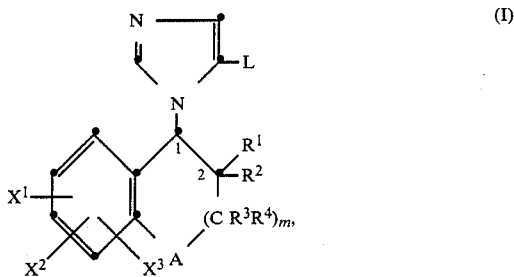

the stereochemically isomeric forms thereof, and the salts thereof, have useful herbicidal properties. The substituents $R^1$, $R^2$, $R^3$, $R^4$, $X^1$, $X^2$, $X^3$, A, L and m have the meanings defined herein.

22 Claims, No Drawings

HERBICIDAL IMIDAZOLE DERIVATIVES

The present invention relates to novel herbicidally active 1,5-substituted imidazole derivatives, to agrochemical compositions containing these compounds, and to a method for controlling weeds, preferably for selectively controlling weeds in crops of useful plants. The invention relates also to processes for the preparation of the novel compounds.

The invention relates to herbicidally active 1,5-substituted imidazole derivatives corresponding to the formula I

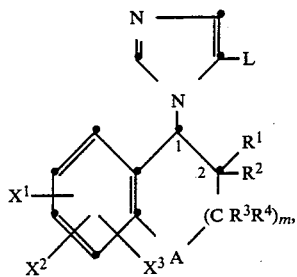

the stereochemically isomeric forms thereof, and salts thereof, in which m is 0 or 1, A is a group

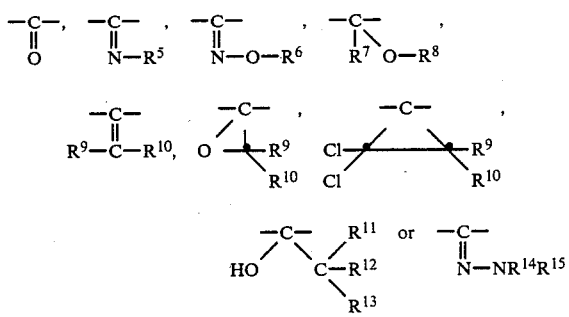

or if m is 0, also a group

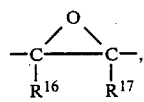

L is a cyano or a group

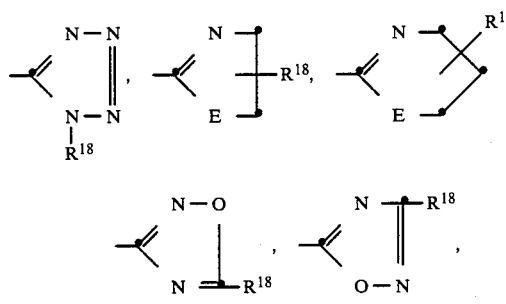

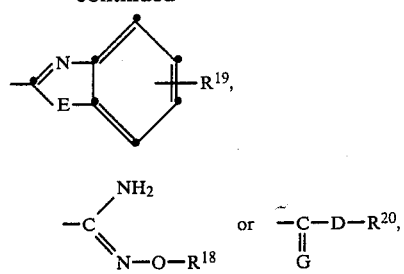

$X^1$ is hydrogen, $C_1$-$C_5$alkyl, $C_1$-$C_5$alkoxy, halogen, $C_2$-$C_5$alkenyl, nitro, amino, $C_1$-$C_5$alkylcarbonylamino, trifluoromethyl or difluoromethoxy, $X^2$ is hydrogen, $C_1$-$C_5$alkyl, halogen or $C_1$-$C_5$alkoxy, $X^3$ is hydrogen or halogen, each of $R^1$ and $R^2$, independently of the other, is hydrogen, $C_1$-$C_5$alkyl or $C_2$-$C_5$alkenyl, or $R_1$ and $R^2$ together with the carbon atom carrying them form a spirocyclic $C_3$-$C_7$cycloalkane ring, $R^3$ is hydrogen, $C_1$-$C_5$alkyl, halogen, $C_1$-$C_5$alkoxy or hydroxy, $R^4$ is hydrogen, $C_1$-$C_5$alkyl, halogen or $C_1$-$C_5$alkoxy, or $R^3$ and $R^4$ together with the carbon atom carrying them form a carbonyl group, or $R^2$ and $R^3$ are a $C_2$-$C_5$alkylene bridge, wherein each of $R^5$, $R^6$, $R^7$, $R^9$ and $R^{16}$ is hydrogen, $C_1$-$C_5$alkyl, —$CH_2$—$C_2$-$C_5$alkenyl, benzyl or phenyl, $R^8$ is hydrogen, —CO—$R^{21}$ or —$SO_2$—$R^{22}$, each of $R^{10}$, $R^{11}$, $R^{12}$ and $R^{17}$, independently of the others, is hydrogen, $C_1$-$C_5$alkyl, $C_2$-$C_5$alkenyl or phenyl, $R^{13}$ is hydrogen, halogen, $C_1$-$C_5$alkoxy, amino, $C_1$-$C_5$alkylamino or di-$C_1$-$C_5$alkylamino, each of $R^{14}$ and $R^{15}$, kindependently of the other, is hydrogen or $C_1$-$C_5$alkyl, E is oxygen, sulfur or —$NR^{18}$—, $R^{18}$ is hydrogen or $C_1$-$C_5$alkyl, $R^{19}$ is hydrogen, $C_1$-$C_5$alkyl, $C_1$-$C_5$alkoxy, halogen, nitro, trifluoromethyl or difluoromethoxy, G is oxygen, sulfur or =N—$R^{20}$, D is oxygen, sulfur,

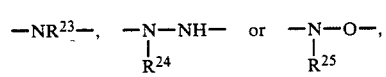

each of $R^{20}$, $R^{23}$, $R^{24}$ and $R^{25}$, independently of the others, is hydrogen, $C_1$-$C_5$alkyl, —$CH_2$—$C_2$-$C_5$alkenyl, —$CH_2$—$C_2$—$C_6$alkynyl, $C_3$-$C_7$-cycloalkyl, or $C_1$-$C_5$alkyl substituted by $C_3$-$C_7$cycloalkyl, $C_3$-$C_7$cycloalkoxy, phenyl, $C_1$-$C_5$alkoxy, hydroxy, cyano,

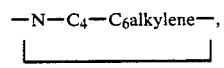

carboxy or by $C_1$-$C_5$alkoxycarbonyl, or $R^{20}$ and $R^{23}$ together with the nitrogen atom carrying them form an unsubstituted or $C_1$-$C_5$alkyl-substituted piperidinyl, pyrrolidinyl, morpholinyl or thiomorpholinyl ring, $R^{21}$ is $C_1$-$C_5$alkyl that is unsubstituted or substituted by $C_1$-$C_5$alkoxy or by from 1 to 3 halogen atoms, or is phenyl that is unsubstituted or substituted by 1 or 2 substituents from the group $C_1$–$C_5$alkyl, $C_1$–$C_5$-alkoxy, halogen, $C_1$–$C_5$haloalkyl, $C_1$–$C_5$-Haloalkoxy, nitro and benzyl, and $R^{22}$ is $C_1$–$C_5$alkyl, $C_1$–$C_5$haloalkyl, or phenyl that is unsubstituted or substituted by 1 or 2 substituents from the group $C_1$–$C_5$alkyl, $C_1$–$C_5$-alkoxy, $C_1$–$C_5$-haloalkyl, $C_1$–$C_5$haloalkoxy, halogen and nitro.

Imidazolecarboxylic acid esters having partially hydrogenated, condensed polycyclic substituents are known, together with their biological activity and methods of preparation, from European Patent Application EP-A-207563.

Surprisingly, the compounds of formula I according to the invention have strong herbicidal properties which allow the control of weeds. The importance of this property is increased by the fact that some useful plant crops are not damaged by treatment with compounds of formula I or that very slight damage to the crop occurs only when very high dosages are used. The compounds of formula I are therefore valuable selective herbicides in crops of useful plants such as cereal, sugar beet, rape, soybeans, rice and maize. A wide range of application rates can be used particularly in rice crops, especially when the rice crops concerned are transplanted rice and the compounds of formula I are applied after transplantation.

The active ingredients of formula I are customarily used at application rates of from 0.01 to 5.0 kg of active ingredient per hectare in order to achieve satisfactory results. Where environmental conditions require it, the application rates may in suitable cases exceed the limits indicated above. The preferred application rates are, however, generally from 0.02 kg to 1.0 kg of active ingredient per hectare.

In the definitions, alkyl is to be understood as being straight-chain or branched alkyl, for example methyl, ethyl, n-propyl, isopropyl, or the four butyl isomers, or the isomers that can be formed with the limitation of up to 5 carbon atoms. Alkoxy is to be understood as being: methoxy, ethoxy, propoxy, the four butoxy isomers and the pentyloxy isomers, but especially methoxy, ethoxy or isopropoxy.

In the above definitions, halogen is fluorine, chlorine, bromine or iodine, with fluorine and chlorine being preferred. Alkenyl is, for example, vinyl, 1-propenyl, 1-methylpropenyl, 1-butenyl, allyl, vinyl, 1-propenyl, 1-methylpropenyl, 1-butenyl, 3-butenyl, 2-butenyl, 2-pentenyl, 3-pentenyl, 1-pentenyl, methallyl or 3-methyl-2-butenyl, with allyl and methallyl being preferred. Examples of alkynyl are ethynyl, propargyl, 1-propynyl, 1-butynyl, 2-butynyl, 3-butynyl, 2-pentynyl, 3-pentynyl or 4-pentynyl, but preferably propargyl. Cycloalkyl is generally cyclopropyl, cyclobutyl, cyclopentyl, cyclohexyl or cycloheptyl, preferably cyclopentyl or cyclohexyl.

The ring members defined under A correspond essentially to the structural elements derivable from the carbonyl function, such as the imine function, the oxime function, the hydrazone function, the exocyclic alkylidene function, the oxirane function, the dichlorocyclopropane function and the hydroxy function, and the dehydrate and oxirane functions that can be derived therefrom in turn.

In the case where $R^2$ and $R^3$ together form an alkylene bridge, these two substituents produce fused, saturated hydrocarbon rings which have a common bond with the saturated ring containing ring member A.

The groups falling within the scope of the definition of L are carboxylic acid derivatives, such as carboxylic acid esters, carboxylic acid nitriles, carboxylic acid amides, carbonimidic acids, carboxylic acid hydrazides, amidoximes, hydroxamic acids, amidines and the various cyclised derivatives of these functions, such as tetralines, oxazolines, oxazines, oxadiazoles or benzoxazoles, and the corresponding derivatives of thiocarboxylic acids or dithiocarboxylic acids.

The invention relates also to the salts that can be formed by the compounds of formula I with organic or inorganic bases, such as amines, alkali metal bases and alkaline earth metal bases, or quaternary ammonium bases or with organic or inorganic acids, such as mineral acids, sulfonic acids, carboxylic acids or phosphorus-containing acids.

Examples of salt-forming mineral acids are hydrofluoric acid, hydrochloric acids, hydrobromic acid, hydriodic acid, sulfuric acid, nitric acid, chloric acid, perchloric acid or phosphoric acid. Preferred salt-forming sulfonic acids are toluenesulfonic acids, benzenesulfonic acid, methanesulfonic acid or trifluoromethanesulfonic acid. Preferred salt-forming carboxylic acids are acetic acid, trifluoroacetic acid, benzoic acid, chloroacetic acid, phthalic acid, maleic acid, malonic acid and citric acid. Phosphorus-containing acids are the various phosphonic acids, phosphonous acids and phosphinic acids.

Preferred salt-forming alkali metal hydroxides and alkaline earth metal hydroxides are the hydroxides of lithium, sodium potassium, magnesium or calcium, but especially those of sodium or potassium. Examples of suitable salt-forming amines are primary, secondary and tertiary aliphatic and aromatic amines, suchas methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, but especially isopropylamine, diethanolamine and 1,4-diazabicyclo[2.2.2]-octane. Examples of quaternary ammonium bases are generally the cations of haloammonium salts, for example the tetramethylammonium cation, the trimethylbenzylammonium cation, the tetraethylammonium cation, the trimethylethylammonium cation and also the ammonium cation.

The invention includes all optical isomers of compounds of formula I and any diastereoisomers which may occur. Diastereoisomers may be present in the isomeric mixtures when the compounds of formula I contain more than one asymmetrically substituted carbon atom. Unless defined otherwise, the chemical names of compounds include mixtures of stereochemically isomeric forms. The mixtures contain where appropriate all diastereoisomers and enantiomers of the underlying molecular structure.

The pure isomeric forms of these optically active compounds can be obtained from the mixtures by customary separation methods. If, in an individual case, a specific stereochemical form is desired, this compound is preferably prepared by stereoselective synthesis processes. In these processes it is advantageous to use pure forms of the optically active starting materials.

Preferred compounds of formula I are those in which either (a) $X^2$ and $X^3$ are hydrogen, or (b) $X^1$ is hydrogen, chlorine, methyl or methoxy, or (c) L is —COOR$^{20}$ or —CONR$^{20}$R$^{23}$, or
(d) each of R$^1$, R$^2$, R$^3$ and R$^4$, independently of the others, is hydrogen or methyl, or
(e) A is the group

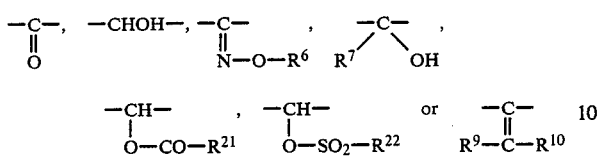

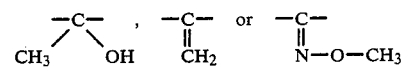

wherein each of R$^6$, R$^7$, R$^9$ and R$^{10}$, independently of the others, is hydrogen, C$_1$–C$_5$alkyl or phenyl, R$^{21}$ is C$_1$–C$_5$alkyl, C$_1$–C$_5$chloroalkyl, C$_2$–C$_4$alkoxyalkyl or phenyl, and R$^{22}$ is C$_1$–C$_5$alkyl, or phenyl that is unsubstituted or substituted by methyl, chlorine or by nitro.

Especially preferred compounds of sub-group (c) are those in which L is carboxy, carbamoyl, C$_1$–C$_5$alkoxycarbonyl, C$_1$–C$_5$alkylcarbamoyl, di-C$_1$–C$_5$-alkylcarbamoyl or C$_1$–C$_5$alkoxycarbamoyl.

Special mention is made of those compounds in which L is methoxycarbonyl, ethoxycarbonyl, methylcarbamoyl or methoxycarbamoyl.

Preferred compounds of sub-group (e) are those in which A is the group

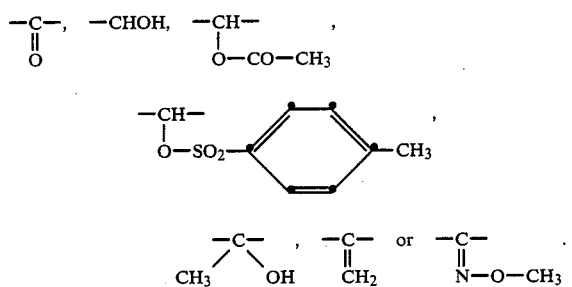

An especially preferred group of compounds of formula I comprises the compounds in which X$^1$ is hydrogen, chlorine, methyl or methoxy, X$^2$ is hydrogen, methyl or methoxy, X$^3$ is hydrogen, L is the group —COOR$^{20}$ or —CONR$^{20}$R$^{23}$, each of R$^1$, R$^2$, R$^3$ and R$^4$, independently of the others, is hydrogen or methyl and A is the group

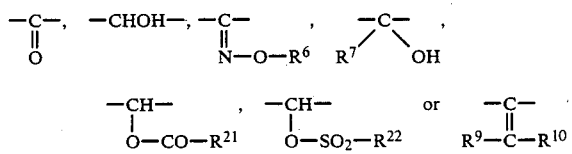

wherein each of R$^6$, R$^7$, R$^9$ and R$^{10}$, independently of the others, is hydrogen, C$_1$–C$_5$alkyl or phenyl, R$^{21}$ is C$_1$–C$_5$alkyl, C$_1$–C$_5$chloroalkyl, C$_2$–C$_4$alkoxyalkyl or phenyl, and R$^{22}$ is C$_1$–C$_5$alkyl, or phenyl that is unsubstituted or substituted by methyl, chlorine or by nitro.

Of these compounds, special mention should be made of those in which L is carboxy, carbamoyl, C$_1$–C$_5$alkoxycarbonyl, C$_1$–C$_5$alkylcarbamoyl, di-C$_1$–C$_5$-alkylcarbamoyl or C$_1$–C$_5$alkoxycarbamoyl, and A is the group

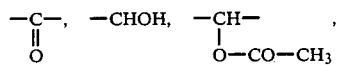

but especially those in which L is methoxycarbonyl, ethoxycarbonyl, methylcarbamoyl or methoxycarbamoyl.

The following preferred individual compounds of the present invention may be mentioned:

1-(2,2-dimethyl-3-oxoindan-1-yl)-5-imidazolecarboxylic acid methyl ester, 1-(2,2-dimethyl-4-oxotetralin-1-yl)-5-imidazolecarboxylic acid methyl ester, 1,3-trans-1-(3-bromo-2,2-dimethyl-4-oxotetralin-1-yl)-5-imidazolecarboxylic acid methyl ester, 1,3-cis-1-(3-bromo-2,2-dimethyl-4-oxotetralin-1-yl)-5-imidazolecarboxylic acid methyl ester, 1,4-trans-1-(2,2-dimethyl-4-hydroxytetralin-1-yl)-5-imidazolecarboxylic acid methyl ester, 1,3-cis-1-(2,2-dimethyl-3-hydroxyindan-1-yl)-5-imidazolecarboxylic acid methyl ester, 1,3-trans-1-(2,2-dimethyl-3-hydroxyindan-1-yl)-5-imidazolecarboxylic acid methyl ester, 1,4-cis-1-(4-acetoxy-2,2-dimethyltetralin-1-yl)-5-imidazolecarboxylic acid methyl ester, 1,4-trans-1-(4-acetoxy-2,2-dimethyltetralin-1-yl)-5-imidazolecarboxylic acid methyl ester, and 1-(2,2-dimethyl-3-methylidenylindan-1-yl)-5-imidazolecarboxylic acid methyl ester.

The compounds of formula I according to the invention are generally prepared in accordance with the following methods known per se.

The compounds of sub-formula Ia

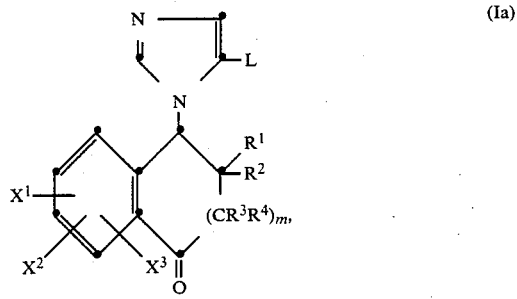

in which L is cyano or C$_1$–C$_5$alkoxycarbonyl and R$^1$, R$^2$, R$^3$, R$^4$, X$^1$, X$^2$, X$^3$ and m have the meanings given under formula I, are obtained by oxidising a compound of formula II

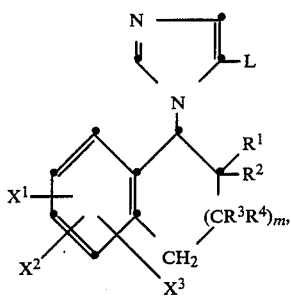

(II)

in which $R^1$, $R^2$, $R^3$, $R^4$, $X^1$, $X^2$, $X^3$, L and m have the meanings given under formula Ia, with an oxidising agent.

Oxidising agents that have proved especially suitable for this reaction are potassium permanganate and ammonium peroxodisulfate. The oxidation is preferably carried out in dilute aqueous mineral acids, such as sulfuric acid, nitric acid or hydrochloric acid. When using ammonium peroxodisulfate, the oxidising operation can be facilitated and accelerated by the addition of catalytic amounts of silver nitrate. The reaction temperature is from 0° C. to +120° C., preferably from +40° C. to +100° C., especially from +50° C. to +80° C. The oxidation can, however, also be carried out in organic solvents with the aid of organic peracids. Suitable oxidation systems are, for example, 3-chloroperbenzoic acid, perbenzoic acid or monoperphthalic acid in methylene chloride or chloroform. Peracetic acid in glacial acetic acid or performic acid in formic acid are also suitable. The reaction temperature is preferably from −20° C. to +60° C., especially from −10° C. to +30° C. The starting materials of formula II are known from EP-A-207 563.

The compounds of sub-formula Ib

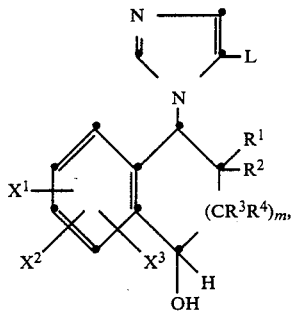

(Ib)

in which $R^1$, $R^2$, $R^3$, $R^4$, $X^1$, $X^2$, $X^3$, L and m have the meanings given under formula Ia, are obtained from the corresponding compounds of formula Ia preferably by reduction of the carbonyl function.

Suitable reducing agents are characterised by their selectivity towards the carbonyl function. Reducing agents having specific selective reducing capacity are shown in the literature. Sodium borohydride and lithium borohydride have proved especially suitable in the described process. The reduction operation is advantageously carried out in an inert polar solvent, such as an alcohol, ether or hydrocarbon, for example methanol, ethanol, isopropanol, diethyl ether, tetrahydrofuran, dioxan, cyclohexane, benzene, toluene or xylene. The reaction temperature is generally from −10° C. to +70° C., preferably from 0° C. to +50° C.

The compounds of sub-formula Ic

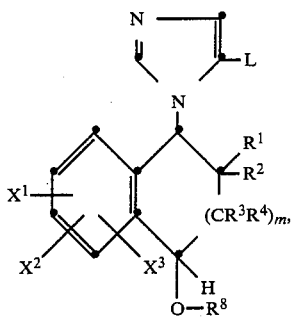

(Ic)

in which $R^1$, $R^2$, $R^3$, $R^4$, $X^1$, $X^2$, $X^3$, L and m have the meanings given under formula Ia and $R^8$ is the radical —CO—$R^{21}$ or —SO$_2$—$R^{22}$, are obtained by acylation of compounds of formula Ib with an acyl halide or acid anhydride of formula III, IV, V or VI Hal—CO—$R^{21}$ (III)

$R^{21}$—CO—O—CO—$R^{21}$ (IV)

Hal—SO$_2$—$R^{22}$ (V)

$R^{22}$—SO$_2$—O—SO$_2$—$R^{22}$ (VI)

in which $R^{21}$ and $R^{22}$ have the meanings given under formula I and Hal is fluorine, chlorine or bromine, but preferably chlorine, in the presence of a base.

Both inorganic and organic bases are suitable bases. Preferred bases are those which dissolve in the inert organic solvent that is advantageously used, and therefore organic amines are especially suitable for use in the said process. Such amines are tertiary aliphatic and aromatic amines, such as trimethylamine, triethylamine, tripropylamine, quinuclidine, pyridine, quinoline and isoquinoline. Preferred amines are triethylamine and especially 1,4-diazabicyclo[2.2.2]octane. Suitable inorganic bases are carbonates or hydrogen carbonates of alkali metals or alkaline earth metals. Suitable inert organic solvents are: ethers or hydrocarbons, such as diethyl ether, dioxan, tetrahydrofuran, benzene, cyclohexane, hexane, xylenes or toluene. The raction temperature is not a critical factor and can be varied within a wide range. It is generally from −20° C. to +120° C., preferably from 0° C. to +80° C.

The compounds of sub-formula Id

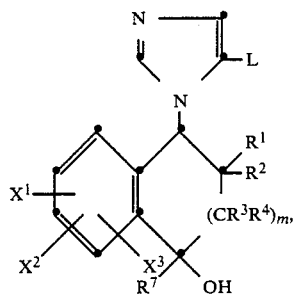

(Id)

in which $R^1$, $R^2$, $R^3$, $R^4$, $X^1$, $X^2$, $X^3$, L and m have the meanings given under formula Ia and $R^7$ is $C_1$-$C_5$alkyl, —CH$_2$—C$_2$-C$_5$alkenyl, benzyl or phenyl, are obtained from the compounds of formula Ia by reaction with a reagent of formula VII

  (VII)

in which Hal is bromine or iodine and R$^7$ has the meaning given under formula Id. If desired, the free hydroxy function can be converted with the acylating reagents of formula III, IV, V or VI into those derivatives of formula I in which A is the group

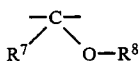

in which R$^7$ and R$^8$ have a meaning other than hydrogen. The reaction conditions for the acylation correspond to those for the preparation of compounds of sub-formula Ic. This reaction (II+VII→Id) corresponds to the Grignard type known in the literature and is carried out under the conditions customary for such reactions in an anhydrous ethereal solvent. Typical reactions take place in diethyl ether, dioxan or tetrahydrofuran at a temperature of from 0° C. to +80° C., preferably from +10° C. to +50° C.

If the compounds of formula Id in which R$^7$ is C$_1$-C$_5$alkyl, benzyl or —CH$_2$—C$_2$-C$_5$alkenyl are reacted with dehydrating reagents, such as, for example, trifluoromethanesulfonic acid anhydride in pyridine, then depending upon the substitution at the vicinal carbon atom, a double bond in the ring or an exocyclic double bond will be obtained. If the vicinal ring member carbon atom is not substituted by a hydrogen atom, then the exocyclic double bond will be obtained, i.e. compounds of formula Ie

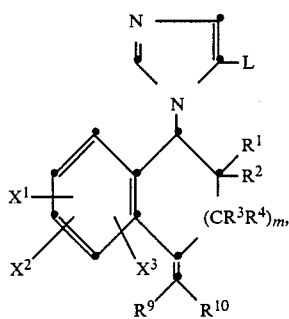  (Ie)

in which R$^1$, R$^2$, R$^3$, R$^4$, X$^1$, X$^2$, X$^3$, L and m have the meanings given under formula Ia and R$^9$ and R$^{10}$ have the meanings given under formula I, will be obtained.

If the vicinal ring member carbon atom is substituted by a hydrogen atom and if m is 1, then the described dehydration will yield also intermediates of the 1,2-dihydronaphthalene type formula VIII

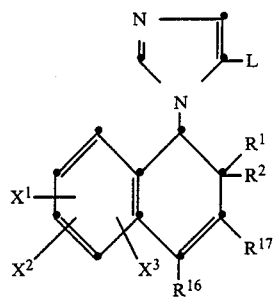  (VIII)

in which R$^1$, R$^2$, R$^3$, R$^4$, X$^1$, X$^2$, X$^3$ and L have the meanings given under formula Ia and R$^{16}$ and R$^{17}$ have the meanings given under formula I. These intermediates of formula VIII are converted by oxidation with peracids into the compounds of sub-formula If

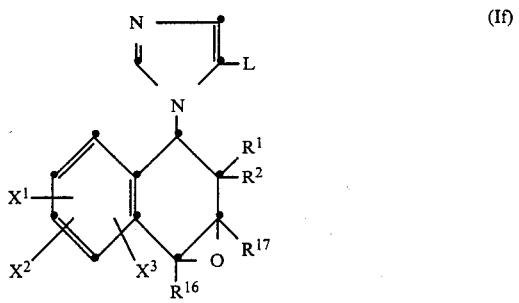  (If)

according to the invention, in which R$^1$, R$^2$, R$^3$, R$^4$, X$^1$, X$^2$, X$^3$ and L have the meanings given under formula Ia and R$^{16}$ and R$^{17}$ have the meanings given under formula I.

The dehydration reactions (Id→Ic and Id→VIII) are preferably carried out at a temperature of from −20° C. to +50° C., especially from +10° C. to +30° C. Preferred dehydration systems are, for example: trifluoromethanesulfonic acid anhydride in pyridine at from −40° C. to −30° C.; p-toluenesulfonic acid chloride in pyridine at from +10° C. to +20° C.; methanesulfonic acid chloride in triethylamine and ethyl acetate at from −30° C. to −20° C.; concentrated hydrobromic acid (48%) at from +20° C. to +50° C.

The epoxidation of intermediates of formula VIII is effected by reaction with organic peracids. Examples of these reagents are performic acid, peracetic acid, or mixtures of formic acid or acetic acid with hydrogen peroxide; perbenzoic acid, 3chloroperbenzoic acid or monoperphthalic acid. For better control of the reaction it is advantageously carried out in an organic solvent. Examples are carboxylic acids, such as formic acid or acetic acid, or chlorinated hydrocarbons, such as carbon tetrachloride, chloroform or methylene chloride. The reaction temperature is customarily from −20° C. to +40° C., preferably from −10° C. to +20° C.

The compounds of sub-formula Ig

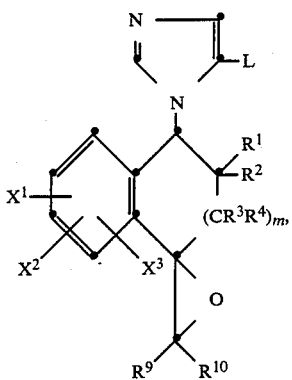 (Ig)

in which $R^1$, $R^2$, $R^3$, $R^4$, $R^9$, $R^{10}$, $X^1$, $X^2$, $X^3$, L and m have the meanings given under formula Ie, are obtained from compounds of formula Ie by epoxidation with peracids.

The reaction conditions for reaction Ie→Ig correspond to those for the reaction of VIII→If.

The compounds of sub-formula Ih

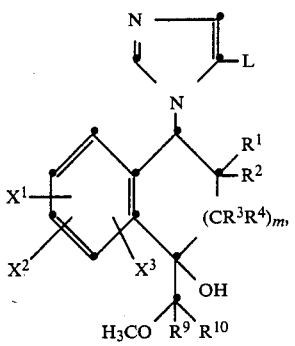 (Ih)

in which $R^1$, $R^2$, $R^3$, $R^4$, $R^9$, $R^{10}$, $X^1$, $X^2$, $X^3$, L and m have the meanings given under formula Ie, are obtained by treatment of the epoxides of formula Ig with methanol in the presence of a base.

In a typical reaction the epoxide of formula Ig is reacted in a methanolic solution containing equivalent amounts of alkali metal, preferably sodium or potassium. The reaction temperature is generally from 0° C. to +60° C., preferably from +10° C. to +30° C.

The compounds of sub-formula Ii

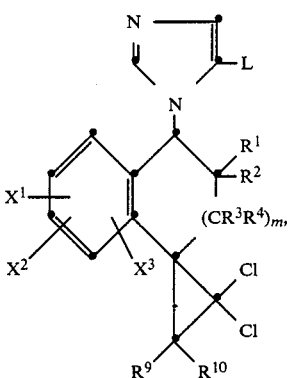 (Ii)

in which $R^1$, $R^2$, $R^3$, $R^4$, $R^9$, $R^{10}$, $X^1$, $X^2$, $X^3$, L and m have the meanings given under formula Ie, are obtained by reacting the compound of formula Ie with dichlorocarbene.

Dichlorocarbene is generally produced in reaction solutions in situ. In a customary procedure the compound of formula Ie is dissolved in chloroform, and to this solution there is added as a second phase 30% aqueous alkali metal hydroxide solution. Vigorous stirring and the addition of a phase transfer catalyst promote the addition of the dichlorocarbene to the exocyclic double bond. A large number of reactions of this type are known in the literature. The phase transfer catalysts generally used are quaternary ammonium salts, such as tetraethylammonium bromide, tetraethylammonium chloride or iodide, tetrabutylammonium chloride, bromide or iodide, triethylbenzylammonium chloride, bromide or iodide, and other tetraalkylammonium halides. The reaction temperature is usually from −20° C. to +80° C., preferably from 0° C. to +30° C.

By treatment with 48% hydrobromic acid in dimethyl sulfoxide at a temperature of from +20° C. to +130° C., preferably from +50° C. to +100° C. there are obtained from compounds of formula Ia those derivatives in which the α-position is brominated, that is to say in the case where m is 1, $R^3$ or $R^4$ is then bromine.

The imino compounds of sub-formula Ij

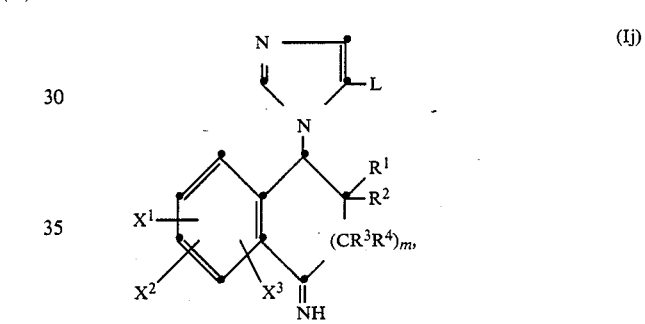 (Ij)

in which $R^1$, $R^2$, $R^3$, $R^4$, $X^1$, $X^2$, $X^3$, L and m have the meanings given under formula Ia, are obtained from the substances of formula Ia by reaction with the compound of formula IX

$(C_6H_5)_3P=N-Si(CH_3)_3$ (IX)

in an inert hydrocarbon, such as benzene, toluene or xylene, at a temperature of from −20° C. to +60° C., preferably from 0° C. to +20° C.

The compounds of sub-formula Ik

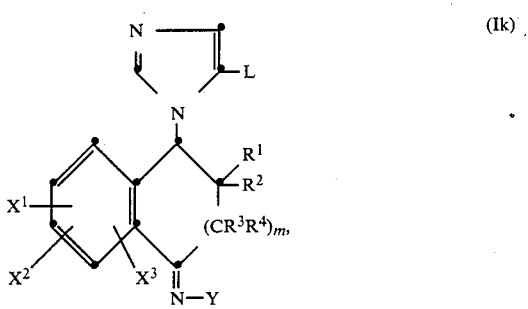 (Ik)

in which $R^1$, $R^2$, $R^3$, $R^4$, $X^1$, $X^2$, $X^3$, L and m have the meanings given under formula Ia and Y is $C_1$-$C_5$alkyl, $-CH_2-C_2$-$C_5$alkenyl, benzyl, phenyl, $-O-R^6$ or $-NR^{14}R^{15}$, are obtained from the compounds of formula Ia by condensation with the corresponding amine compounds of formula X $$H_2N—Y \qquad (X)$$

in which Y is $C_1$-$C_5$alkyl, —$CH_2$—$C_2$-$C_5$alkenyl, benzyl, phenyl, —O—$R^6$ or —$NR^{14}R^{15}$ and $R^6$, and $R^{15}$ have the meanings given under formula I.

The reaction (Ia→Ik) is a condensation reaction which takes place with the elimination of water. The reaction conditions for this condensation are described many times in the literature and in some cases differ widely in the choice of solvents and reaction temperatures.

In the present reaction (Ia→Ik) it has proved especially advantageous to select a polar solvent, such as pyridine, at a temperature of from $-30°$ C. to $+40°$ C., preferably from $-10°$ C. to $-30°$ C.

The reagents and starting materials required for the preparation of the various sub-groups Ia to Ik are described in the literature and the majority are commercially available.

Compounds Ia to Ik can, if desired, be converted by customary derivatising methods into the derivative covered by L in formula I.

In the derivatisation the alkoxycarbonyl radical L is modified in known manner, for example by hydrolysis, esterification, transesterification, amidation, transamidation or oximation.

The cyano compound (L=—CN) is obtained by dehydrating the carboxylic acid amide (L=—$CONH_2$). Suitable agents for this purpose are, for example, phosphorus pentachloride, phosphorus oxychloride, thienyl chloride, phosphorus pentoxide and acetic anhydride. The reaction temperature depends upon the choice of dehydrating agent and is generally from $+20°$ C. to $+120°$ C. If desired, it is also possible to add inert organic solvents. The esters, thiol esters or amide derivatives (X=—CO—D—$R^{20}$) can be prepared from the carboxylic acids (L=—COOH) or the activated compounds obtainable therefrom, such as acid halides or anhydrides or mixed anhydrides, by reaction with the corresponding alcohols, thiols or amine compounds. Esters and thiol esters may also be obtained by alkylation of the carboxylic acids with haloalkyl compounds in the presences of bases. The tetrazoles can be obtained by reaction of the nitriles (L=—CN) with azides in organic solvents, such as dimethylformamide or dimethyl sulfoxide, at a temperature of from $+20°$ C. to $+150°$ C. The other heterocyclic compounds of formula I having the groups

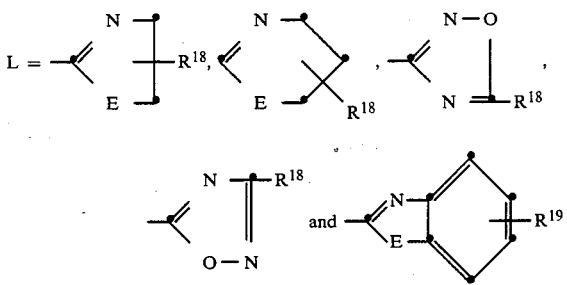

can be obtained by reaction of the corresponding carboxylic acids, or their activated representatives, such as their acid halides, with bifunctional compounds such as diamines, amino alcohols, aminothiols or amidoximes, according to processes known per se. The thiono esters (L=—CS—D—$R^{20}$) can be obtained from the corresponding oxygen compounds by reaction with phosphorus pentasulfide, advantageously in the presence of bases, in organic solvents, such as dimethylformamide, acetonitrile, toluene or xylene. The amidoximes (L=

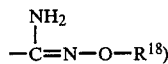

are obtained from the nitriles by reaction with hydroxylamine and can be converted into the other derivatives ($R^{18}$=alkyl) by reaction with alkylating agents.

If the synthesis of stereochemically pure isomers is required, it is advisable to select stereoselective reaction steps and conditions. Conversely, pure isomers can often be separated from the isomeric mixture by customary separating methods, or can be obtained in pure form by the use of pure optically active starting materials.

The compounds of formula I are stable and do not require special precautions for handling.

When the compounds of formula I are used within the indicated range of application rates, these active ingredients are distinguished by good selective herbicidal properties which render them excellently suitable for use in crops of useful plants, especially sugar beet, soybeans, cereals and maize, and more especially rice. In some cases damage is caused even to weeds which could previously be eliminated only by the use of total herbicides. If application rates far exceeding the recommended range are used, then the development of all the plants treated is damaged to such an extent that the plants die.

The invention relates also to herbicidal compositions that contain the novel compounds of formula I. The invention relates also to methods of controlling weeds by the use of those novel active ingredients.

The compounds of formula I are used in unmodified form or, preferably, in the form of compositions together with the adjuvants conventionally employed in the art of formulation, and are therefore formulated in known manner e.g. into emulsifiable concentrates, directly sprayable or dilutable solutions, dilute emulsions, wettable powders, soluble powders, dusts, granulates, and also encapsulations in e.g. polymer substances. As with the nature of the compositions, the methods of applications, such as spraying, atomising, dusting, scattering or pouring, are chosen in accordance with the intended objective and the prevailing circumstances.

The fomulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$-alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$-alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily used in the art of formulation are described inter alia in the following publications:

"McCutcheon's Detergents and Emulsifiers Annual", MC Publishing Corp., Ridgewood, N.J., 1981;

H. Stache, "Tensid-Taschenbuch", 2nd Edition, C. Hanser Verlag, Munich, Vienna, 1981;

M. and J. Ash, "Encyclopaedia of Surfactants", Vol. I-III, Chemical Publishing Co., New York, 1980-1981.

The agrochemical compositions usually contain 0.1 to 95%, preferably 0.1 to 80%, of a compound of formula I, 1 to 99.9% of a solid or liquid adjuvant, and 0 to 25%, perferably 0.1 to 25%, of a surfactant.

Preferred formulations have especially the following compositions: (thoughout percentages are by weight).

| Emulsifiable concentrates: | | |
|---|---|---|
| active ingredient: | 1 to 20%, preferably | 5 to 10% |
| surfactant: | 5 to 30%, preferably | 10 to 20% |
| liquid carrier: | 50 to 94%, preferably | 70 to 85% |
| Dusts: | | |
| active ingredient: | 0.1 to 10%, preferably | 0.1 to 1% |
| solid carrier: | 99.9 to 90%, preferably | 99.9 to 99% |
| Suspension concentrates: | | |
| active ingredient: | 5 to 75%, preferably | 10 to 50% |
| water: | 94 to 25%, preferably | 88 to 30% |
| surfactant: | 1 to 40%, preferably | 2 to 30% |
| Wettable powder: | | |
| active ingredient: | 0.5 to 90%, preferably | 1 to 80% |
| surfactant: | 0.5 to 20%, preferably | 1 to 15% |
| solid carrier: | 5 to 99%, preferably | 15 to 90% |
| Granulates: | | |
| active ingredient: | 0.5 to 30%, preferably | 3 to 15% |
| solid carrier: | 99.5 to 70%, preferably | 97 to 85%. |

Whereas commercial products will preferably be formulated as concentrates, the end user will normally employ dilute formulations. The forms of application can be diluted down to 0.001% active ingredient.

The following Examples illustrate the present invention but do not represent a limitation thereof. The preparation examples show the methods by which the novel compounds of formula I can be obtained. The biological examples and the formulation examples demonstrate the use of the active ingredients for agrochemical purposes.

PREPARATION EXAMPLES

EXAMPLE P1

1-(2,2-dimethyl-3-oxoindan-1-yl)-5-imidazolecarboxylic acid methyl ester

A mixture of 30.0 g of 1-(2,2-dimethylindan-1-yl)-5-imidazolecarboxylic acid methyl ester, 150 ml of water and 17 g of sulfuric acid is heated to +80° C. Within a period of 1.5 hours a solution of 114 g of ammonium peroxodisulfate is added dropwise thereto. When the reaction is complete, the solution is cooled to +7° C. and adjusted to pH 3 by the addition of 30% sodium hydroxide solution. The solution is extracted twice using 200 ml of methylene chloride each time, and the organic phase is dried over sodium sulfate and concentrated to dryness by evaporation. The residue is taken up in a small amount of methylene chloride, and ether is added. The resulting suspension is filtered, the filtrate is concentrated by evaporation and the residue is crystallised from an ether/hexane mixture. 19 g of 1-(2,2-dimethyl-3-oxoindan-1-yl)-5-imidazolecarboxylic acid methyl ester having a melting point of 104°-108° C. are obtained.

EXAMPLE P2

1-(2,2,3-trimethyl-3-hydroxyindan-1-yl)-5-imidazolecarboxylic acid methyl ester

A solution of methylmagnesium iodide is prepared from 1.7 g of magnesium chips and 11 g of methyl iodide in 40 ml of ether. This solution is added dropwise to a solution of 10 g of 1-(2,2-dimethyl-3-oxoindan-1-yl)-5-carboxylic acid methyl ester in 300 ml of ether and 150 ml of tetrahydrofuran. The pasty suspension is stirred for a further 10 minutes, and then saturated ammonium sulfate solution is added until phase separation takes place. The organic phase is separated off, dried over sodium sulfate and concentrated by evaporation. The residue is purified by chromatography on silica gel, yielding 4.2 g of 1-(2,2,3-trimethyl-3-hydroxyindan-1-yl)-5-imidazolecarboxylic acid methyl ester having a melting point of 149°-152° C.

EXAMPLE P3

1-(2,2-dimethyl-3-methylideneindan-1-yl)-5-imidazolecarboxylic acid methyl ester 1.7 ml of trifluoromethanesulfonic acid anhydride are added dropwise at a temperature of −15° C. to a solution of 2.5 g of 1-(2,2,3-trimethyl-3-hydroxyindan-1-yl)-5-imidazolecarboxylic acid methyl ester in 20 ml of pyridine. After a reaction period of 10 minutes the mixture is concentrated by evaporation in vacuo and the residue is chromatographed on silica gel using an ether/methylene chloride mixture (1:1). 1.2 g of 1-(2,2-dimethyl-3-methylideneindan-1-yl)-5-imidazolecarboxylic acid methyl ester are obtained in the form of brownish colourless crystals having a melting point of 125°-126° C.

EXAMPLE P4

1-(2,2-dimethyl-4-oxotetralin-1-yl)-5-imidazolecarboxylic acid methyl ester 142 g of 1-(2,2-dimethyltetralin-1-yl)-5-imidazolecarboxylic acid methyl ester are suspended in 1 liter of distilled water. The suspension is heated to +87° C. and, while stirring, a total of 335 g of ammonium peroxodisulfate is added in portions thereto within a period of 1.5 hours in such a manner that the temperature does not exceed +90° C. After the reaction mixture has been cooled to +15° C., the pH value is adjusted to pH 4 by the addition of approximately 335 g of 30% sodium hydroxide solution and the whole is extracted with 500 ml of methylene chloride. The organic phase is separated off, dried over sodium sulfate, treated with activated carbon and concentrated by evaporation. Crystallisation of the residue from ether yields 42 g of 1-(2,2-dimethyl-4-oxotetralin-1-yl)-5-imidazolecarboxylic acid methyl ester having a melting point of 93°-95° C.

EXAMPLE P5

1-(3-bromo-2,2-dimethyl-4-oxotetralin-1-yl)-5-imidazolecarboxylic acid methyl ester 3.0 g of 48% hydrobromic acid are added dropwise to a solution of 3.0 g of 1-(2,2-dimethyl-4-oxotetralin-1-yl)-5-imidazolecarboxylic acid methyl ester in 20 ml of dimethyl sulfoxide. The reaction mixture is heated at +95° C. for 30 minutes and after cooling is poured onto 300 ml of ice-water. The product is extracted three times using 100 ml of ether each time. The combined organic phases are washed twice with 2% sodium hydrogen carbonate solution, dried over magnesium sulfate and concentrated by evaporation. The residue is taken up in warm ether and cooled to +10° C. The resulting precipitate is separated off, yielding 1.9 g of 1,3-trans-1-(3-bromo-2,2-dimethyl-4-oxotetralin-1-yl)-5-imidazolecarboxylic acid methyl ester having a melting point of 170°-173° C. The mother liquor is further concentrated by evaporation and yields, by fractional crystallisation, 0.3 g of 1,3-cis-1-(3-bromo-2,2-dimethyl-4-oxotetralin-1-yl)-5-imidazolecarboxylic acid methyl ester having a melting point of 176°-178° C.

EXAMPLE P6

1-(2,2-dimethyl-4-hydroxytetralin-1-yl)-5-imidazolecarboxylic acid methyl ester 4.0 g of sodium borohydride are added at room temperature to a solution of 20.9 g of 1-(2,2-dimethyl-4-oxotetralin-1-yl)-5-imidazolecarboxylic acid methyl ester in 200 ml of methanol and the mixture is stirred at room temperature for 30 minutes. The reaction mixture is concentrated by evaporation and the residue is separated by chromatography on silica gel using an ether/methylene chloride mixture (1:1). 11.0 g of 1,4-trans-1-(2,2-dimethyl-4-hydroxytetralin-1-yl)-5-imidazolecarboxylic acid methyl ester having a melting point of 135°-136° C. and 3.0 g of 1,4-cis-1-(2,2-dimethyl-4-hydroxytetralin-1-yl)-5-imidazolecarboxylic acid methyl ester having a melting point of 179°-180° C. are obtained.

EXAMPLE P7

1,4-trans-1-(4-acetoxy-2,2-dimethyltetralin-1-yl)-5-imidazolecarboxylic acid methyl ester 1.0 g of triethylamine and 0.8 g of acetyl chloride are added to a solution of 1.8 g of 1,4-trans-1-(2,2-dimethyl-4-hydroxytetralin-1-yl)-5-imidazolecarboxylic acid methyl ester in 20 ml of tetrahydrofuran and the mixture is stirred at room temperature for 30 minutes. The triethylammonium chloride that has formed is separated off, the filtrate is concentrated by evaporation and the residue is purified by chromatography on silica gel using an ether/hexane mixture (2:1). 1.0 g of 1,4-trans-1-(4-acetoxy-2,2-dimethyltetralin-1-yl)-5-imidazolecarboxylic acid methyl ester is obtained in the form of a colourless oil.

EXAMPLE P8

1,4-trans-1-(2,2-dimethyl-4-methylsulfonyloxytetralin-1-yl)-5-imidazolecarboxylic acid methyl ester 1 g of triethylamine and 1.8 g of 1,4-trans-1-(2,2-dimethyl-4-hydroxytetralin-1-yl)-5-imidazolecarboxylic acid methyl ester are dissolved in 30 ml of toluene, and 0.8 g of methanesulfonic acid chloride is added. After stirring for 30 minutes at +80° C. the mixture is cooled to room temperature, the triethylammonium chloride that has formed is filtered off and the filtrate is concentrated by evaporation. Subsequent purification by chromatography on silica gel using ether/hexane (3:1) as eluant yields 1.2 g of 1,4-trans-1-(2,2-dimethyl-4-methylsulfonyloxytetralin-1-yl)-5-imidazolecarboxylic acid methyl ester in the form of a colourless resin.

EXAMPLE P9

1-(3,4-epoxy-2,2-dimethyltetralin-1-yl)-5-imidazolecarboxylic acid methyl ester (a) 1-(1,2-dihydro-2,2-dimethylnaphthalen-1-yl)-5-imidazolecarboxylic acid methyl ester 0.9 g of 1,4-trans-1-(2,2-dimethyl-4-methylsulfonyloxytetralin-1-yl)-5-imidazolecarboxylic acid methyl ester is stirred in 5 ml of pyridine for 30 minutes at +60° C. The pyridine is then extensively evaporated off in vacuo and the residue is purified by chromatography on silica gel, a methylene chloride/ether mixture (30:1) being used as eluant. 0.4 g of 1-(1,2-dihydro-2,2-dimethylnaphthalen-1-yl)-5-imidazolecarboxylic acid methyl ester having a melting point of 60°-61° C. is obtained.

(b) 9.4 g of 55% 3-chloroperbenzoic acid are added to a solution of 8.5 g of 1-(1,2-dihydro-2,2-dimethylnaphthalen-1-yl)-5-imidazolecarboxylic acid methyl ester in 150 ml of methylene chloride and the mixture is stirred at room temperature for 2 hours. The precipitate is separated off and the filtrate is washed twice using 50 ml of sodium hydrogen carbonate solution (5%) each time, dried over magnesium sulfate and concentrated by evaporation. Chromatography of the residue on silica gel [eluant: ether/hexane (3:1)] yields 1.7 g of a mixture of 1,4-cis-1-(3,4-epoxy-2,2-dimethyltetralin-1-yl)-5-imidazolecarboxylic acid methyl ester and 1,4-trans-1-(3,4-epoxy-2,2-dimethyltetralin-1-yl)-5-imidazolecarboxylic acid methyl ester in a ratio of 1:1 (m.p. 60°-68° C.).

EXAMPLE P10

1-(1,2-dihydro-2,2-dimethylnaphthalen-1-yl)-5-imidazolecarboxylic acid methyl ester One-step process for the preparation of the intermediate prepared according to Examples P8 and P9(a).

5 ml of triethylamine are added dropwise at room temperature to a mixture of 1.8 g of methanesulfonic acid chloride and 5.2 g of 1,4-trans-1-(2,2-dimethyl-4-hydroxytetralin-1-yl)-5-imidazolecarboxylic acid methyl ester in 100 ml of ethyl acetate. After a reaction period of 1 hour, the resulting precipitate is separated off and the supernatant solution is concentrated by evaporation. The residue is purified by chromatography on silica gel using an ether/methylene chloride mixture (1:1). 2.5 g of 1-(1,2-dihydro-2,2-dimethylnaphthalen-1-yl)-5-imidazolecarboxylic acid methyl ester having a melting point of 60°-62° C. are obtained.

EXAMPLE P11

1-(2,2-dimethyl-4-oxotetralin-1-yl)-5-imidazolecarboxylic acid methyl ester 10.6 g of 3-chloroperbenzoic acid are added to a solution, cooled to 0° C., of 7.1 g of 1-(2,2-dimethyltetralin-1-yl)-5-imidazolecarboxylic acid methyl ester in 200 ml of methylene chloride. The mixture is stirred at room temperature for a further 72 hours. A solution of 7.5 g of sodium hydrogen carbonate in 100 ml of water is then added. The organic phase is separated off, washed with water, dried and concentrated by evaporation. The residue is purified by column chromatography on silica gel using chloroform as eluant. The product-containing fraction is again chromatographed on silica gel using a chloroform/methanol mixture (99.5:0.5). 0.3 g of 1-(2,2-dimethyl-4-oxotetralin-1-yl)-5-imidazolecarboxylic acid methyl ester is obtained in the form of a solid.

The intermediates and end products listed in Tables 1 to 15 below are obtained in analogous manner.

TABLE 1

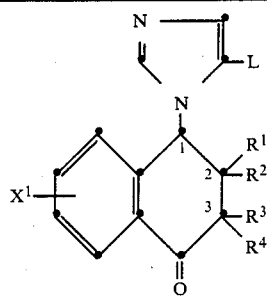

| Comp. No. | $R^1$ | $R^2$ | $R^3$ | $R^4$ | $X^1$ | L | physical data |
|---|---|---|---|---|---|---|---|
| 1.01 | H | H | H | H | H | COOCH$_3$ | m.p. 90-92° C. |
| 1.02 | C$_2$H$_5$ | C$_2$H$_5$ | CH$_3$ | H | H | COOCH$_3$ | |
| 1.03 | CH$_3$ | H | H | H | H | COOCH$_3$ | 1,2-cis |
| 1.04 | CH$_3$ | H | H | H | H | COOCH$_3$ | 1,2-trans |
| 1.05 | CH$_3$ | CH$_3$ | H | H | H | COOCH$_3$ | m.p. 103-105° C. |
| 1.06 | CH$_3$ | CH$_3$ | H | H | H | COOC$_2$H$_5$ | |
| 1.07 | CH$_3$ | CH$_3$ | H | H | H | COOC$_4$H$_9$—t | resin |
| 1.08 | CH$_3$ | CH$_3$ | CH$_3$ | H | H | COOCH$_3$ | 1,3-cis |
| 1.09 | CH$_3$ | CH$_3$ | CH$_3$ | H | H | COOCH$_3$ | 1,3-trans |

TABLE 1-continued

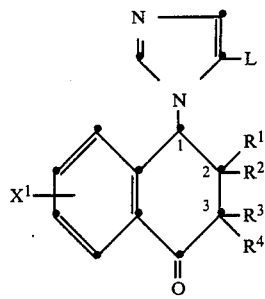

| Comp. No. | R¹ | R² | R³ | R⁴ | X¹ | L | physical data |
|---|---|---|---|---|---|---|---|
| 1.10 | H | H | CH₃ | H | H | COOCH₃ | 1,3-cis |
| 1.11 | H | H | CH₃ | H | H | COOCH₃ | 1,3-trans |
| 1.12 | H | H | CH₃ | CH₃ | H | COOCH₃ | |
| 1.13 | CH₃ | H | CH₃ | H | H | COOCH₃ | 2,3-cis |
| 1.14 | CH₃ | H | CH₃ | H | H | COOCH₃ | 2,3-trans |
| 1.15 | H | —(CH₂)₃— | | H | H | COOCH₃ | |
| 1.16 | CH₃ | CH₃ | H | H | H | CONHCH₃ | |
| 1.17 | CH₃ | CH₃ | H | H | H | CONH—OCH₃ | |
| 1.18 | CH₃ | CH₃ | H | H | 7-CH₃ | COOCH₃ | |
| 1.19 | CH₃ | CH₃ | H | H | 7-Cl | COOCH₃ | |
| 1.20 | CH₃ | CH₃ | H | H | 5-Cl | COOCH₃ | |
| 1.21 | CH₃ | CH₃ | Br | H | H | COOCH₃ | 1,3-trans, m.p. 170–173° C. |
| 1.22 | CH₃ | CH₃ | Br | H | H | COOCH₃ | 1,3-cis, m.p. 176–178° C. |
| 1.23 | CH₃ | CH₃ | H | H | H | COOH | m.p. 240° C. (decomp.) |

TABLE 2

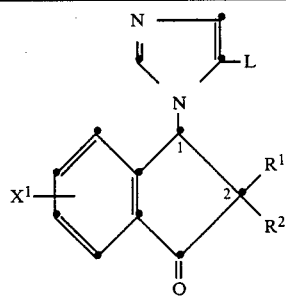

| Comp. No. | R¹ | R² | X¹ | L | physical data |
|---|---|---|---|---|---|
| 2.01 | CH₃ | CH₃ | H | COOCH₃ | m.p. 119–121° C. |
| 2.02 | CH₃ | CH₃ | H | COOC₂H₅ | |
| 2.03 | C₄H₉—t | H | H | COOCH₃ | |
| 2.04 | CH₃ | CH₃ | H | CONHCH₃ | |
| 2.05 | CH₃ | CH₃ | H | CONH—OCH₃ | |
| 2.06 | C₂H₅ | C₂H₅ | H | COOCH₃ | |

TABLE 2-continued

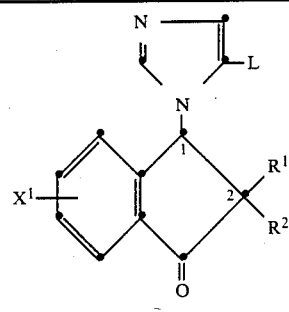

| Comp. No. | R¹ | R² | X¹ | L | physical data |
|---|---|---|---|---|---|
| 2.07 | CH₃ | CH₃ | 6-CH₃ | COOCH₃ | |
| 2.08 | CH₃ | CH₃ | 6-Cl | COOCH₃ | |
| 2.09 | CH₃ | CH₃ | 6-OCH₃ | COOCH₃ | |
| 2.10 | —(CH₂)₄— | | H | COOCH₃ | |
| 2.11 | —(CH₂)₅— | | H | COOCH₃ | |

TABLE 3

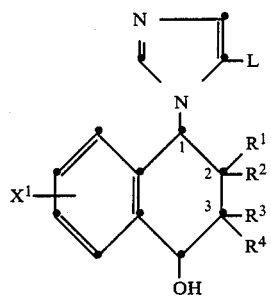

| Comp. No. | R¹ | R² | R³ | R⁴ | X¹ | L | physical data |
|---|---|---|---|---|---|---|---|
| 3.01 | H | H | H | H | H | COOCH$_3$ | 1,4-trans, m.p. 131–134° C. |
| 3.02 | C$_2$H$_5$ | C$_2$H$_5$ | CH$_3$ | H | H | COOCH$_3$ | |
| 3.03 | CH$_3$ | H | H | H | H | COOCH$_3$ | 1,2-cis |
| 3.04 | CH$_3$ | H | H | H | H | COOCH$_3$ | 1,2-trans |
| 3.05 | CH$_3$ | CH$_3$ | H | H | H | COOCH$_3$ | 1,4-trans, m.p. 135–136° C. |
| 3.06 | CH$_3$ | CH$_3$ | H | H | H | COOC$_2$H$_5$ | |
| 3.07 | CH$_3$ | CH$_3$ | H | H | H | COOC$_4$H$_9$—t | |
| 3.08 | CH$_3$ | CH$_3$ | CH$_3$ | H | H | COOCH$_3$ | 1,3-cis |
| 3.09 | CH$_3$ | CH$_3$ | CH$_3$ | H | H | COOCH$_3$ | 1,3-trans |
| 3.10 | H | H | CH$_3$ | H | H | COOCH$_3$ | 1,3-cis |
| 3.11 | H | H | CH$_3$ | H | H | COOCH$_3$ | 1,3-trans |
| 3.12 | H | H | CH$_3$ | CH$_3$ | H | COOCH$_3$ | |
| 3.13 | CH$_3$ | H | CH$_3$ | H | H | COOCH$_3$ | 2,3-cis |
| 3.14 | CH$_3$ | H | CH$_3$ | H | H | COOCH$_3$ | 2,3-trans |
| 3.15 | H | —(CH$_2$)$_3$— | | H | H | COOCH$_3$ | |
| 3.16 | CH$_3$ | CH$_3$ | H | H | H | CONHCH$_3$ | |
| 3.17 | CH$_3$ | CH$_3$ | H | H | H | CONH—OCH$_3$ | |
| 3.18 | CH$_3$ | CH$_3$ | H | H | 7-CH$_3$ | COOCH$_3$ | |
| 3.19 | CH$_3$ | CH$_3$ | H | H | 7-Cl | COOCH$_3$ | |
| 3.20 | CH$_3$ | CH$_3$ | H | H | 5-Cl | COOCH$_3$ | |
| 3.21 | CH$_3$ | CH$_3$ | H | H | H | COOCH$_3$ | 1,4-cis, m.p. 179–180° C. |
| 3.22 | H | H | H | H | H | COOCH$_3$ | 1,4-cis, m.p. 150–154° C. |

TABLE 4

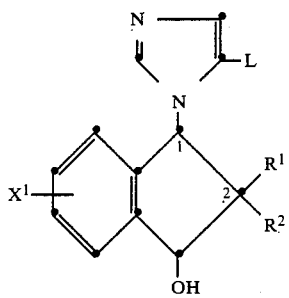

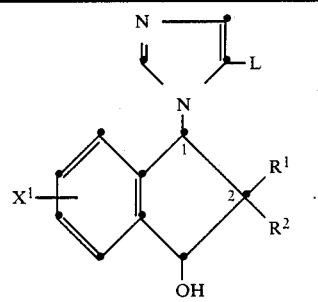

| Comp. No. | R¹ | R² | X¹ | L | physical data |
|---|---|---|---|---|---|
| 4.01 | CH$_3$ | CH$_3$ | H | COOCH$_3$ | 1,3-cis, m.p. 194–195° C. |
| 4.02 | CH$_3$ | CH$_3$ | H | COOC$_2$H$_5$ | |
| 4.03 | C$_4$H$_9$—t | H | H | COOCH$_3$ | |
| 4.04 | CH$_3$ | CH$_3$ | H | CONHCH$_3$ | |
| 4.05 | CH$_3$ | CH$_3$ | H | CONH—OCH$_3$ | |
| 4.06 | C$_2$H$_5$ | C$_2$H$_5$ | H | COOCH$_3$ | |
| 4.07 | CH$_3$ | CH$_3$ | 6-CH$_3$ | COOCH$_3$ | |
| 4.08 | CH$_3$ | CH$_3$ | 6-Cl | COOCH$_3$ | |
| 4.09 | CH$_3$ | CH$_3$ | 6-OCH$_3$ | COOCH$_3$ | |
| 4.10 | —(CH$_2$)$_4$— | | H | COOCH$_3$ | |
| 4.11 | —(CH$_2$)$_5$— | | H | COOCH$_3$ | |
| 4.12 | CH$_3$ | CH$_3$ | H | COOCH$_3$ | 1,3-trans, m.p. 145–146° C. |

TABLE 5

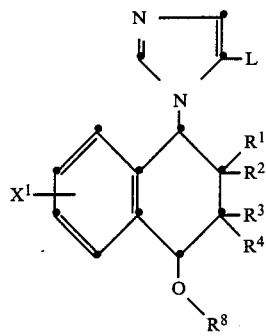

| Comp. No. | R¹ | R² | R³ | R⁴ | X¹ | R⁸ | L | physical data |
|---|---|---|---|---|---|---|---|---|
| 5.01 | H | H | H | H | H | COCH$_3$ | COOCH$_3$ | 1,4-cis |
| 5.02 | H | H | H | H | H | COCH$_3$ | COOCH$_3$ | 1,4-trans |
| 5.03 | H | H | H | H | H | COCH$_2$Cl | COOCH$_3$ | 1,4-trans |
| 5.04 | H | H | H | H | H | COCH$_2$—OCH$_3$ | COOCH$_3$ | 1,4-trans |
| 5.05 | H | H | H | H | H | COC$_6$H$_5$ | COOCH$_3$ | |
| 5.06 | CH$_3$ | CH$_3$ | H | H | H | COCH$_3$ | COOCH$_3$ | 1,4-cis, oil |
| 5.07 | CH$_3$ | CH$_3$ | H | H | H | COCH$_3$ | COOCH$_3$ | 1,4-trans, oil |
| 5.08 | CH$_3$ | CH$_3$ | H | H | H | COC$_2$H$_5$ | COOCH$_3$ | |
| 5.09 | CH$_3$ | CH$_3$ | H | H | H | COCH$_2$Cl | COOCH$_3$ | |
| 5.10 | CH$_3$ | CH$_3$ | H | H | H | COCH$_3$ | COOC$_2$H$_5$ | |
| 5.11 | CH$_3$ | CH$_3$ | H | H | H | COCH$_3$ | COOC$_4$H$_9$—t | |
| 5.12 | CH$_3$ | H | H | H | H | COCH$_3$ | COOCH$_3$ | |
| 5.13 | CH$_3$ | H | H | H | H | COCH$_2$Cl | COOCH$_3$ | |
| 5.14 | CH$_3$ | H | H | H | H | COCH$_2$—OCH$_3$ | COOCH$_3$ | |
| 5.15 | CH$_3$ | H | H | H | H | COC$_6$H$_5$ | COOCH$_3$ | |
| 5.16 | H | H | H | H | H | SO$_2$CH$_3$ | COOCH$_3$ | 1,4-trans |
| 5.17 | H | H | H | H | H | SO$_2$—C$_6$H$_4$—4-CH$_3$ | COOCH$_3$ | 1,4-cis |
| 5.18 | H | H | H | H | H | SO$_2$CH$_3$ | COOCH$_3$ | 1,4-cis |
| 5.19 | H | H | H | H | H | SO$_2$—C$_6$H$_4$—4-CH$_3$ | COOCH$_3$ | 1,4-trans |
| 5.20 | H | H | H | H | H | SO$_2$—C$_6$H$_5$ | COOCH$_3$ | |
| 5.21 | CH$_3$ | CH$_3$ | H | H | H | SO$_2$—C$_6$H$_4$—4-CH$_3$ | COOCH$_3$ | 1,4-trans, oil |
| 5.22 | CH$_3$ | CH$_3$ | H | H | H | SO$_2$—C$_6$H$_4$—4-CH$_3$ | COOCH$_3$ | 1,4-cis, oil |
| 5.23 | CH$_3$ | CH$_3$ | H | H | H | SO$_2$CH$_3$ | COOCH$_3$ | |
| 5.24 | CH$_3$ | CH$_3$ | H | H | H | SO$_2$—C$_6$H$_5$ | COOCH$_3$ | |
| 5.25 | CH$_3$ | CH$_3$ | H | H | H | SO$_2$CH$_3$ | COOC$_2$H$_5$ | |
| 5.26 | CH$_3$ | CH$_3$ | H | H | H | SO$_2$CH$_3$ | COOC$_4$H$_9$—t | |
| 5.27 | CH$_3$ | H | H | H | H | SO$_2$CH$_3$ | COOCH$_3$ | |
| 5.28 | CH$_3$ | H | H | H | H | SO$_2$—C$_6$H$_4$—4-CH$_3$ | COOCH$_3$ | |
| 5.29 | CH$_3$ | H | H | H | H | SO$_2$—C$_6$H$_5$ | COOCH$_3$ | |
| 5.30 | CH$_3$ | H | H | H | H | SO$_2$—C$_6$H$_4$—2-NO$_2$ | COOCH$_3$ | |

TABLE 6

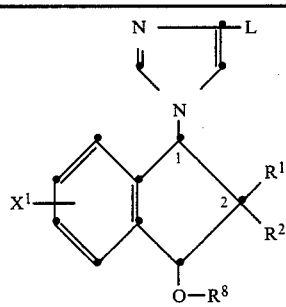

| Comp. No. | R¹ | R² | X¹ | R⁸ | L | physical data |
|---|---|---|---|---|---|---|
| 6.01 | CH$_3$ | CH$_3$ | H | COCH$_3$ | COOCH$_3$ | 1,3-trans |
| 6.02 | CH$_3$ | CH$_3$ | H | COCH$_3$ | COOCH$_3$ | 1,3-cis |
| 6.03 | CH$_3$ | CH$_3$ | H | COC$_2$H$_5$ | COOCH$_3$ | resin |
| 6.04 | CH$_3$ | CH$_3$ | H | COCH$_2$Cl | COOCH$_3$ | |
| 6.05 | CH$_3$ | CH$_3$ | H | COCH$_3$ | COOC$_2$H$_5$ | |
| 6.06 | CH$_3$ | H | H | COCH$_3$ | COOCH$_3$ | |
| 6.07 | CH$_3$ | H | H | COCH$_2$Cl | COOCH$_3$ | |
| 6.08 | CH$_3$ | H | H | COCH$_2$—OCH$_3$ | COOCH$_3$ | |
| 6.09 | CH$_3$ | CH$_3$ | H | SO$_2$CH$_3$ | COOCH$_3$ | |
| 6.10 | CH$_3$ | CH$_3$ | H | SO$_2$—C$_6$H$_4$—4-CH$_3$ | COOCH$_3$ | |
| 6.11 | CH$_3$ | CH$_3$ | H | SO$_2$—C$_6$H$_5$ | COOCH$_3$ | |

TABLE 6-continued

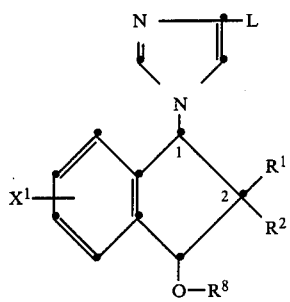

| Comp. No. | R¹ | R² | X¹ | R⁸ | L | physical data |
|---|---|---|---|---|---|---|
| 6.12 | CH₃ | CH₃ | H | SO₂—C₆H₄—2-NO₂ | COOCH₃ | |
| 6.13 | CH₃ | CH₃ | H | SO₂CH₃ | COOC₂H₅ | |
| 6.14 | CH₃ | H | H | SO₂CH₃ | COOCH₃ | |
| 6.15 | CH₃ | H | H | SO₂—C₆H₄—4-CH₃ | COOCH₃ | |
| 6.16 | CH₃ | H | H | SO₂—C₆H₅ | COOCH₃ | |

TABLE 7

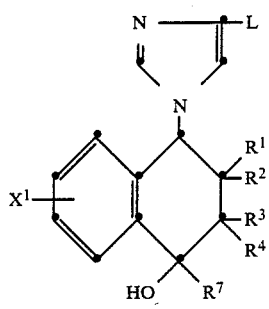

| Comp. No. | R¹ | R² | R³ | R⁴ | X¹ | R⁷ | L | physical data |
|---|---|---|---|---|---|---|---|---|
| 7.01 | H | H | H | H | H | CH₃ | COOCH₃ | |
| 7.02 | H | H | H | H | H | C₂H₅ | COOCH₃ | |
| 7.03 | H | H | H | H | H | C₃H₇—n | COOCH₃ | |
| 7.04 | H | H | H | H | H | C₃H₇—i | COOCH₃ | |
| 7.05 | H | H | H | H | H | C₆H₅ | COOCH₃ | |
| 7.06 | CH₃ | CH₃ | H | H | H | C₂H₅ | COOCH₃ | |
| 7.07 | CH₃ | CH₃ | H | H | H | CH₃ | COOCH₃ | m.p. 186–189° C. |
| 7.08 | CH₃ | CH₃ | H | H | H | C₃H₇—i | COOCH₃ | |
| 7.09 | CH₃ | CH₃ | H | H | H | C₃H₇—n | COOCH₃ | |
| 7.10 | CH₃ | CH₃ | H | H | H | CH₃ | COOC₂H₅ | |
| 7.11 | CH₃ | CH₃ | H | H | H | CH₃ | COOC₄H₉—t | |
| 7.12 | CH₃ | H | H | H | H | CH₃ | COOCH₃ | |
| 7.13 | CH₃ | H | H | H | H | C₆H₅ | COOCH₃ | |
| 7.14 | CH₃ | H | H | H | H | C₃H₇—i | COOCH₃ | |
| 7.15 | CH₃ | H | H | H | H | C₃H₇—n | COOCH₃ | |

TABLE 8

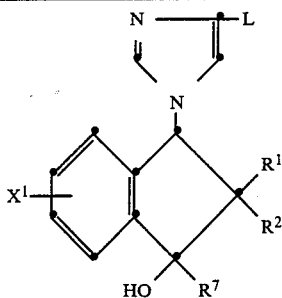

| Comp. No. | R¹ | R² | X¹ | R⁷ | L | physical data |
|---|---|---|---|---|---|---|
| 8.01 | CH₃ | CH₃ | H | C₂H₅ | COOCH₃ | |
| 8.02 | CH₃ | CH₃ | H | CH₃ | COOCH₃ | m.p. 149–152° C. |
| 8.03 | CH₃ | CH₃ | H | C₃H₇—n | COOCH₃ | |
| 8.04 | CH₃ | CH₃ | H | C₃H₇—i | COOCH₃ | |
| 8.05 | CH₃ | CH₃ | H | C₃H₇—i | COOC₂H₅ | |
| 8.06 | CH₃ | H | H | C₃H₇—i | COOCH₃ | |
| 8.07 | CH₃ | H | H | C₂H₅ | COOCH₃ | |
| 8.08 | CH₃ | H | H | CH₃ | COOCH₃ | |
| 8.09 | CH₃ | H | H | CH₃ | COOCH₃ | 1,2-cis |
| 8.10 | CH₃ | H | H | CH₃ | COOCH₃ | 1,2-trans |

TABLE 9

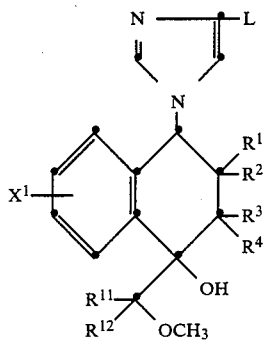

| Comp. No. | R¹ | R² | R³ | R⁴ | X¹ | R¹¹ | R¹² | L | physical data |
|---|---|---|---|---|---|---|---|---|---|
| 9.01 | H | H | H | H | H | H | H | COOCH₃ | |
| 9.02 | H | H | H | H | H | CH₃ | CH₃ | COOCH₃ | |
| 9.03 | H | H | H | H | H | C₂H₅ | H | COOCH₃ | |
| 9.04 | H | H | H | H | H | C₆H₅ | H | COOCH₃ | |
| 9.05 | H | H | H | H | H | C₂H₅ | C₂H₅ | COOCH₃ | |
| 9.06 | CH₃ | CH₃ | H | H | H | H | H | COOCH₃ | |
| 9.07 | CH₃ | CH₃ | H | H | H | CH₃ | CH₃ | COOCH₃ | |
| 9.08 | CH₃ | CH₃ | H | H | H | C₂H₅ | C₆H₅ | COOCH₃ | |
| 9.09 | CH₃ | CH₃ | H | H | H | C₆H₅ | C₆H₅ | COOCH₃ | |
| 9.10 | CH₃ | CH₃ | H | H | H | H | H | COOC₂H₅ | |
| 9.11 | CH₃ | CH₃ | H | H | H | H | H | COOC₄H₉—t | |
| 9.12 | CH₃ | H | H | H | H | CH₃ | CH₃ | COOCH₃ | |
| 9.13 | CH₃ | H | H | H | H | H | H | COOCH₃ | |
| 9.14 | CH₃ | H | H | H | H | C₆H₅ | C₆H₅ | COOCH₃ | |
| 9.15 | CH₃ | H | H | H | H | C₆H₅ | H | COOCH₃ | |

TABLE 10

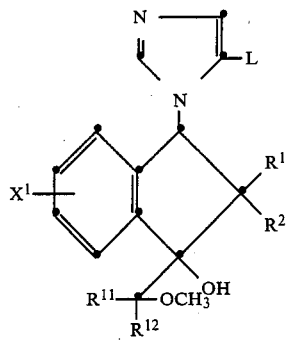

| Comp. No. | R¹ | R² | X¹ | R¹¹ | R¹² | L | physical data |
|---|---|---|---|---|---|---|---|
| 10.01 | CH₃ | CH₃ | H | H | H | COOCH₃ | |
| 10.02 | CH₃ | CH₃ | H | CH₃ | CH₃ | COOCH₃ | |
| 10.03 | CH₃ | CH₃ | H | C₆H₅ | C₆H₅ | COOCH₃ | |
| 10.04 | CH₃ | CH₃ | H | C₆H₅ | H | COOCH₃ | |
| 10.05 | CH₃ | CH₃ | H | H | H | COOC₂H₅ | |
| 10.06 | CH₃ | H | H | CH₃ | CH₃ | COOCH₃ | |
| 10.07 | CH₃ | H | H | H | H | COOCH₃ | |
| 10.08 | CH₃ | H | H | C₂H₅ | H | COOCH₃ | |

TABLE 11

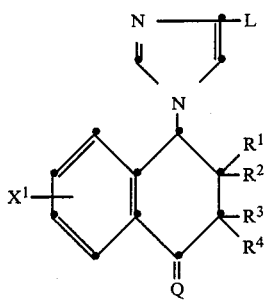

| Comp. No. | R¹ | R² | R³ | R⁴ | X¹ | Q | L | physical data |
|---|---|---|---|---|---|---|---|---|
| 11.01 | H | H | H | H | H | $CH_2$ | $COOCH_3$ | |
| 11.02 | H | H | H | H | H | $C(CH_3)_2$ | $COOCH_3$ | |
| 11.03 | H | H | H | H | H | $CH-C_2H_5$ | $COOCH_3$ | |
| 11.04 | H | H | H | H | H | $CH-C_6H_5$ | $COOCH_3$ | |
| 11.05 | H | H | H | H | H | $C(C_2H_5)_2$ | $COOCH_3$ | |
| 11.06 | $CH_3$ | $CH_3$ | H | H | H | $C(CH_3)_2$ | $COOCH_3$ | |
| 11.07 | $CH_3$ | $CH_3$ | H | H | H | $CH_2$ | $COOCH_3$ | |
| 11.08 | $CH_3$ | $CH_3$ | H | H | H | $CH-C_2H_5$ | $COOCH_3$ | |
| 11.09 | $CH_3$ | $CH_3$ | H | H | H | $C(C_6H_5)_2$ | $COOCH_3$ | |
| 11.10 | $CH_3$ | $CH_3$ | H | H | H | $CH_2$ | $COOC_2H_5$ | |
| 11.11 | $CH_3$ | $CH_3$ | H | H | H | $CH_2$ | $COOC_4H_9-t$ | |
| 11.12 | $CH_3$ | H | H | H | H | $C(CH_3)_2$ | $COOCH_3$ | |
| 11.13 | $CH_3$ | H | H | H | H | $CH_2$ | $COOCH_3$ | |
| 11.14 | $CH_3$ | H | H | H | H | $C(C_6H_5)_2$ | $COOCH_3$ | |
| 11.15 | $CH_3$ | H | H | H | H | $CH-C_6H_5$ | $COOCH_3$ | |
| 11.16 | H | H | H | H | H | NH | $COOCH_3$ | |
| 11.17 | H | H | H | H | H | $N-NH_2$ | $COOCH_3$ | |
| 11.18 | H | H | H | H | H | $N-CH_3$ | $COOCH_3$ | |
| 11.19 | H | H | H | H | H | $N-N(CH_3)_2$ | $COOCH_3$ | |
| 11.20 | $CH_3$ | $CH_3$ | H | H | H | $N-CH_3$ | $COOCH_3$ | |
| 11.21 | $CH_3$ | $CH_3$ | H | H | H | $N-NH_2$ | $COOCH_3$ | |
| 11.22 | $CH_3$ | $CH_3$ | H | H | H | $N-N(CH_3)_2$ | $COOCH_3$ | |
| 11.23 | $CH_3$ | H | H | H | H | $N-CH_3$ | $COOCH_3$ | |
| 11.24 | $CH_3$ | H | H | H | H | $N-N(CH_3)_2$ | $COOCH_3$ | |
| 11.25 | $CH_3$ | H | H | H | H | $N-NH_2$ | $COOCH_2$ | |
| 11.26 | H | H | H | H | H | $N-OCH_3$ | $COOCH_3$ | |
| 11.27 | H | H | H | H | H | $N-OC_2H_5$ | $COOCH_3$ | |
| 11.28 | H | H | H | H | H | $N-O-CH_2-CH=CH_2$ | $COOCH_3$ | oil |
| 11.29 | H | H | H | H | H | $N-OC_4H_9-n$ | $COOCH_3$ | |
| 11.30 | H | H | H | H | H | $N-OC_6H_5$ | $COOCH_3$ | |
| 11.31 | $CH_3$ | $CH_3$ | H | H | H | $N-OCH_3$ | $COOCH_3$ | E-form, m.p. 84-88° C. |
| 11.32 | $CH_3$ | $CH_3$ | H | H | H | $N-OC_2H_5$ | $COOCH_3$ | oil |
| 11.33 | $CH_3$ | $CH_3$ | H | H | H | $N-OH$ | $COOCH_3$ | |
| 11.34 | $CH_3$ | $CH_3$ | H | H | H | $N-O-CH_2-CH=CH_2$ | $COOCH_3$ | |
| 11.35 | $CH_3$ | $CH_3$ | H | H | H | $N-OH$ | $COOC_2H_5$ | |
| 11.36 | $CH_3$ | $CH_3$ | H | H | H | $N-OCH_3$ | $CONHCH_3$ | |
| 11.37 | $CH_3$ | $CH_3$ | H | H | H | $N-OCH_3$ | $COOC_4H_9-t$ | |
| 11.38 | $CH_3$ | H | H | H | H | $N-OCH_3$ | $COOCH_3$ | |
| 11.39 | $CH_3$ | H | H | H | H | $N-OH$ | $COOCH_3$ | |
| 11.40 | $CH_3$ | H | H | H | H | $N-OC_2H_5$ | $COOCH_3$ | |
| 11.41 | $CH_3$ | H | H | H | H | $N-O-CH_2-CH=CH_2$ | $COOCH_3$ | |
| 11.42 | $CH_3$ | $CH_3$ | H | H | H | $N-O-C_6H_{13}-n$ | $COOCH_3$ | oil |
| 11.43 | $CH_3$ | $CH_3$ | H | H | H | $N-O-CH_2-C_6H_5$ | $COOCH_3$ | oil |
| 11.44 | $CH_3$ | $CH_3$ | H | H | H | $N-O-C_4H_9-n$ | $COOCH_3$ | oil |
| 11.45 | $CH_3$ | $CH_3$ | H | H | H | $N-O-CH_2-CH=CHCl$ | $COOCH_3$ | oil |
| 11.46 | $CH_3$ | $CH_3$ | H | H | H | $N-OCH_2-CH=CH_2$ | $COOCH_3$ | oil |

TABLE 12

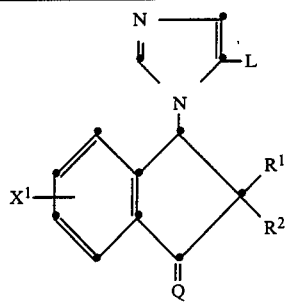

| Comp. No. | R¹ | R² | X¹ | Q | L | physical data |
|---|---|---|---|---|---|---|
| 12.01 | $CH_3$ | $CH_3$ | H | $CH_2$ | $COOCH_3$ | m.p. 125–126° C. |
| 12.02 | $CH_3$ | $CH_3$ | H | $C(CH_3)_2$ | $COOCH_3$ | |
| 12.03 | $CH_3$ | $CH_3$ | H | $C(C_6H_5)_2$ | $COOCH_3$ | |
| 12.04 | $CH_3$ | $CH_3$ | H | $CH-C_6H_5$ | $COOCH_3$ | |
| 12.05 | $CH_3$ | $CH_3$ | H | $CH_2$ | $COOC_2H_5$ | |
| 12.06 | $CH_3$ | H | H | $C(CH_3)_2$ | $COOCH_3$ | |
| 12.07 | $CH_3$ | H | H | $CH_2$ | $COOCH_3$ | |
| 12.08 | $CH_3$ | H | H | $CH-C_2H_5$ | $COOCH_3$ | |
| 12.09 | $CH_3$ | $CH_3$ | H | NH | $COOCH_3$ | |
| 12.10 | $CH_3$ | $CH_3$ | H | $N-NH_2$ | $COOCH_3$ | |
| 12.11 | $CH_3$ | $CH_3$ | H | $N-N(CH_3)_2$ | $COOCH_3$ | |
| 12.12 | $CH_3$ | H | H | $N-CH_3$ | $COOCH_3$ | |
| 12.13 | $CH_3$ | H | H | $N-N(CH_3)_2$ | $COOCH_3$ | |
| 12.14 | $CH_3$ | $CH_3$ | H | $N-OCH_3$ | $COOCH_3$ | oil |
| 12.15 | $CH_3$ | $CH_3$ | H | $N-OH$ | $COOCH_3$ | |
| 12.16 | $CH_3$ | $CH_3$ | H | $N-OC_2H_5$ | $COOCH_3$ | |
| 12.17 | $CH_3$ | $CH_3$ | H | $N-OC_6H_5$ | $COOCH_3$ | |
| 12.18 | $CH_3$ | $CH_3$ | H | $N-OCH_3$ | $COOC_2H_5$ | |
| 12.19 | $CH_3$ | H | H | $N-OCH_3$ | $COOCH_3$ | |
| 12.20 | $CH_3$ | H | H | $N-OH$ | $COOCH_3$ | |
| 12.21 | $CH_3$ | H | H | $N-O-CH_2-CH=CH_2$ | $COOCH_3$ | |
| 12.22 | $CH_3$ | $CH_3$ | H | $N-C_6H_5$ | $COOCH_3$ | resin |
| 12.23 | $CH_3$ | $CH_3$ | H | $N-C_6H_4-4-OCH_3$ | $COOCH_3$ | resin |

TABLE 13

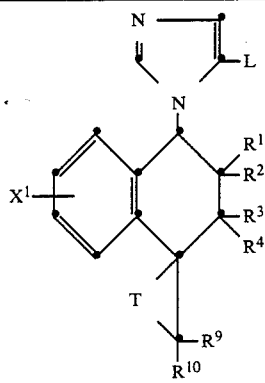

| Comp. No. | R¹ | R² | R³ | R⁴ | X¹ | R⁹ | R¹⁰ | T | L | physical data |
|---|---|---|---|---|---|---|---|---|---|---|
| 13.01 | H | H | H | H | H | H | H | $CCl_2$ | $COOCH_3$ | |
| 13.02 | H | H | H | H | H | $CH_3$ | $CH_3$ | $CCl_2$ | $COOCH_3$ | |
| 13.03 | H | H | H | H | H | $C_2H_5$ | H | $CCl_2$ | $COOCH_3$ | |
| 13.04 | H | H | H | H | H | $C_6H_5$ | H | $CCl_2$ | $COOCH_3$ | |
| 13.05 | H | H | H | H | H | $C_2H_5$ | $C_2H_5$ | $CCl_2$ | $COOCH_3$ | |
| 13.06 | $CH_3$ | $CH_3$ | H | H | H | $CH_3$ | $CH_3$ | $CCl_2$ | $COOCH_3$ | |
| 13.07 | $CH_3$ | $CH_3$ | H | H | H | H | H | $CCl_2$ | $COOCH_3$ | |
| 13.08 | $CH_3$ | $CH_3$ | H | H | H | $C_2H_5$ | H | $CCl_2$ | $COOCH_3$ | |
| 13.09 | $CH_3$ | $CH_3$ | H | H | H | $C_6H_5$ | $C_6H_5$ | $CCl_2$ | $COOCH_3$ | |
| 13.10 | $CH_3$ | $CH_3$ | H | H | H | H | H | $CCl_2$ | $COOC_2H_5$ | |
| 13.11 | $CH_3$ | $CH_3$ | H | H | H | H | H | $CCl_2$ | $COOC_4H_9-t$ | |
| 13.12 | $CH_3$ | H | H | H | H | $CH_3$ | $CH_3$ | $CCl_2$ | $COOCH_3$ | |
| 13.13 | $CH_3$ | H | H | H | H | H | H | $CCl_2$ | $COOCH_3$ | |
| 13.14 | $CH_3$ | H | H | H | H | $C_6H_5$ | $C_6H_5$ | $CCl_2$ | $COOCH_3$ | |
| 13.15 | $CH_3$ | H | H | H | H | $C_6H_5$ | H | $CCl_2$ | $COOCH_3$ | |

TABLE 13-continued

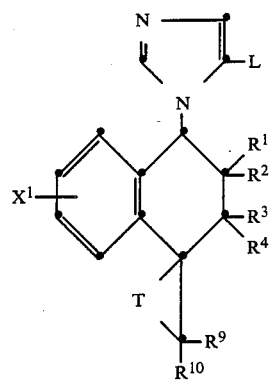

| Comp. No. | R¹ | R² | R³ | R⁴ | X¹ | R⁹ | R¹⁰ | T | L | physical data |
|---|---|---|---|---|---|---|---|---|---|---|
| 13.16 | CH₃ | CH₃ | H | H | H | CH₃ | CH₃ | O | COOCH₃ | |
| 13.17 | H | H | H | H | H | H | H | O | COOCH₃ | |
| 13.18 | H | H | H | H | H | CH₃ | CH₃ | O | COOCH₃ | |
| 13.19 | H | H | H | H | H | C₂H₅ | H | O | COOCH₃ | |
| 13.20 | H | H | H | H | H | C₆H₅ | H | O | COOCH₃ | |
| 13.21 | H | H | H | H | H | C₂H₅ | C₂H₅ | O | COOCH₃ | |
| 13.22 | CH₃ | CH₃ | H | H | H | H | H | O | COOCH₃ | |
| 13.23 | CH₃ | CH₃ | H | H | H | C₂H₅ | H | O | COOCH₃ | |
| 13.24 | CH₃ | CH₃ | H | H | H | C₆H₅ | C₆H₅ | O | COOCH₃ | |
| 13.25 | CH₃ | CH₃ | H | H | H | H | H | O | COOC₂H₅ | |
| 13.26 | CH₃ | CH₃ | H | H | H | H | H | O | CONHCH₃ | |
| 13.27 | CH₃ | CH₃ | H | H | H | H | H | O | COOC₄H₉—t | |
| 13.28 | CH₃ | H | H | H | H | CH₃ | CH₃ | O | COOCH₃ | |
| 13.29 | CH₃ | H | H | H | H | H | H | O | COOCH₃ | |
| 13.30 | CH₃ | H | H | H | H | C₆H₅ | C₆H₅ | O | COOCH₃ | |
| 13.31 | CH₃ | H | H | H | H | C₆H₅ | H | O | COOCH₃ | |

TABLE 14

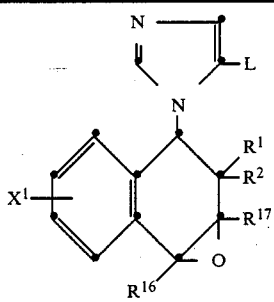

| Comp. No. | R¹ | R² | X¹ | R¹⁶ | R¹⁷ | L | physical data |
|---|---|---|---|---|---|---|---|
| 14.01 | H | H | H | H | H | COOCH₃ | |
| 14.02 | C₂H₅ | C₂H₅ | H | H | CH₃ | COOCH₃ | |
| 14.03 | CH₃ | H | H | H | H | COOCH₃ | |
| 14.04 | CH₃ | H | H | H | H | COOC₂H₅ | m.p. 60–68° C. |
| 14.05 | CH₃ | CH₃ | H | H | H | COOCH₃ | |
| 14.06 | CH₃ | CH₃ | H | H | H | COOC₂H₅ | |
| 14.07 | CH₃ | CH₃ | H | H | H | COOC₄H₉—t | |
| 14.08 | CH₃ | CH₃ | H | H | H | CONHCH₃ | |
| 14.09 | CH₃ | CH₃ | H | H | H | CONH—OCH₃ | |
| 14.10 | CH₃ | CH₃ | H | H | CH₃ | COOCH₃ | |

TABLE 15
(Intermediates)

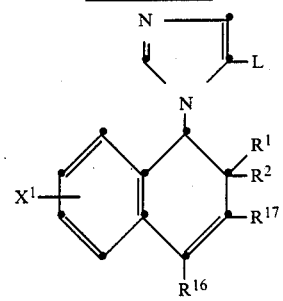

| Comp. No. | R¹ | R² | X¹ | R¹⁶ | R¹⁷ | L | physical data |
|---|---|---|---|---|---|---|---|
| 15.01 | H | H | H | H | H | COOCH₃ | |
| 15.02 | C₂H₅ | C₂H₅ | H | H | CH₃ | COOCH₃ | |
| 15.03 | CH₃ | H | H | H | H | COOCH₃ | |
| 15.04 | CH₃ | H | H | H | H | COOC₂H₅ | |
| 15.05 | CH₃ | CH₃ | H | H | H | COOCH₃ | m.p. 60–62° C. |
| 15.06 | CH₃ | CH₃ | H | H | H | COOC₂H₅ | |
| 15.07 | CH₃ | CH₃ | H | H | H | COOC₄H₉—t | |
| 15.08 | CH₃ | CH₃ | H | H | H | CONHCH₃ | |
| 15.09 | CH₃ | CH₃ | H | H | H | CONH—OCH₃ | |
| 15.10 | CH₃ | CH₃ | H | H | CH₃ | COOCH₃ | |

FORMULATION EXAMPLES

EXAMPLE F1

Formulation Examples for liquid active ingredients of formula I (throughout, percentages are by weight)

| (a) Emulsifiable concentrates | (a) | (b) | (c) |
|---|---|---|---|
| active ingredient No. 5.07 | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any desired concentration can be produced from such concentrates by dilution with water.

| (b) Solutions | (a) | (b) | (c) | (d) |
|---|---|---|---|---|
| active ingredient No. 5.07 | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| petroleum fraction (boiling range 160–100° C.) | — | — | 94% | — |

These solutions are suitable for application in the form of micro-drops.

| (c) Granulates | (a) | (b) |
|---|---|---|
| active ingredient No. 5.06 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| active ingredient No. 5.06 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

EXAMPLE F2

Formulation Examples for solid active ingredients of formula I (throughout, percentages are by weight)

| (a) Wettable powders | (a) | (b) |
|---|---|---|
| active ingredient No. 1.05 | 20% | 60% |
| sodium lignosulfonate | 5% | 5% |
| sodium laurylsulfate | 3% | — |
| sodium diisobutylnaphthalenesulfonate | — | 6% |
| octylphenol polyethylene glycol ether (7–8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | |
|---|---|
| active ingredient No. 1.05 | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| (c) Dusts | (a) | (b) |
|---|---|---|
| active ingredient No. 2.01 | 5% | 8% |
| talcum | 95% | — |
| kaolin | — | 92% |

Ready-for-use dusts are obtained by mixing the active ingredient with the carrier and grinding the mixture in a suitable mill.

| (d) Extruder granulate | |
|---|---|
| active ingredient No. 1.21 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| (e) Coated granulate | |
|---|---|
| active ingredient No. 1.21 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | |
|---|---|
| active ingredient No. 3.05 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

EXAMPLE B1

Pre-emergence herbicidal action

In a greenhouse, immediately after the test plants have been sown in seed trays, the surface of the soil is treated with an aqueous dispersion of the active ingredients obtained from a 25% emulsifiable concentrate. Concentrations of 4 kg of active ingredient/hectare are used. The seed trays are kept in the greenhouse at 22°–25° C. and 50–70% relative humidity and the test is evaluated after 3 weeks.
1: plant has not germinated or has completely died
2–3: very strong action
4–6: moderate action
7–8: weak action
9: no action (as untreated control)

The compounds of Tables 1 to 14 exhibit strong herbicidal action in this test.

Test results: pre-emergence test
Application rate: 4 kg of active ingredient per hectare

| Comp. No. | Avena | Setaria | Sinapis | Stellaria |
|---|---|---|---|---|
| 1.01 | 3 | 2 | 3 | 3 |
| 1.05 | 2 | 1 | 2 | 2 |
| 1.21 | 1 | 1 | 2 | 2 |
| 1.22 | 2 | 1 | 2 | 4 |
| 2.01 | 2 | 1 | 2 | 2 |
| 3.01 | 4 | 2 | 2 | 3 |
| 3.05 | 2 | 1 | 2 | 2 |
| 3.21 | 2 | 1 | 2 | 2 |
| 4.01 | 2 | 1 | 2 | 2 |
| 4.12 | 2 | 1 | 2 | 2 |
| 5.06 | 2 | 1 | 2 | 2 |
| 5.07 | 2 | 1 | 2 | 2 |
| 7.07 | 4 | 2 | 3 | 1 |
| 8.02 | 3 | 1 | 2 | 3 |
| 11.31 | 3 | 1 | 2 | 1 |
| 11.32 | 3 | 2 | 1 | 1 |
| 11.33 | 2 | 3 | 2 | 2 |
| 12.01 | 5 | 1 | 2 | 2 |
| 12.14 | 3 | 2 | 1 | 1 |

EXAMPLE B2

Post-emergence herbicidal action (contact herbicide)

A number of weeds, both mono- and di-cotyledonous, are sprayed postemergence (in the 4- to 6-leaf stage) with an aqueous active ingredient dispersion at a rate of 4 kg of test compound per hectare and kept at 24°–26° C. and 45–60% relative humidity. The test is evaluated 15 days after treatment in accordance with the rating indicated in the preemergence test.

In this test too, the compounds of Tables 1 to 14 exhibit good herbicidal action.

Test results: post-emergence test
Application rate: 4 kg of active ingredient per hectare

| Comp. No. | Avena | Setaria | Lolium | Solanum | Sinapis | Stellaria | Phaseolus |
|---|---|---|---|---|---|---|---|
| 1.01 | 3 | 4 | 4 | 3 | 2 | 4 | 2 |
| 1.21 | 4 | 4 | 3 | 3 | 3 | 3 | 2 |
| 1.22 | 3 | 4 | 4 | 3 | 3 | 2 | 2 |
| 2.01 | 4 | 4 | 3 | 2 | 3 | 4 | 2 |
| 4.01 | 4 | 4 | 4 | 3 | 4 | 5 | 2 |
| 4.12 | 4 | 3 | 4 | 2 | 3 | 4 | 2 |
| 5.06 | 4 | 4 | 4 | 4 | 3 | 4 | 2 |
| 5.07 | 4 | 4 | 4 | 2 | 3 | 4 | 2 |
| 11.31 | 7 | 4 | 6 | 3 | 2 | 3 | 2 |
| 11.32 | 6 | 5 | 4 | 4 | 2 | 3 | 2 |
| 12.01 | 5 | 4 | 4 | 2 | 3 | 3 | 2 |
| 12.14 | 6 | 5 | 4 | 4 | 2 | 3 | 2 |

EXAMPLE B3

Herbicidal action in paddy

The weeds *Echinochloa crus galli* and *Monochoria vaginalis*, which occur in water, are sown in plastic beakers (surface area: 60 cm$^2$; volume: 500 ml). After sowing, the beakers are filled with water up to the surface of the soil. 3 days after sowing, the water level is increased to slightly above the soil surface (3–5 mm). Application is effected 3 days after sowing by spraying the beakers with an aqueous emulsion of the test compounds. The rate of application corresponds to a concentration of 4 kg of active ingredient per hectare (amount of spraying liquor=550 l/ha). The beakers containing the plants are then kept in the greenhouse under optimum growth conditions for rice weeds, i.e. at 25°–30° C. and at high humidity. The evaluation of the test takes place 3 weeks after application, the state of the plants being assessed as in pre-emergence test B1. The compounds of Tables 1 to 14 damage the weeds but not the rice.

Test results: Water weeds
Application rate: 4 kg of active ingredient per hectare

| Comp. No. | Echinochloa | Monochoria |
|---|---|---|
| 1.01 | 1 | 1 |
| 1.05 | 1 | 1 |
| 1.21 | 1 | 1 |
| 1.22 | 1 | 1 |
| 1.23 | 2 | 1 |
| 2.01 | 1 | 1 |
| 3.01 | 1 | 1 |
| 3.05 | 1 | 1 |
| 3.21 | 1 | 1 |
| 3.22 | 1 | 1 |
| 4.01 | 1 | 1 |
| 4.12 | 1 | 1 |
| 5.06 | 1 | 1 |
| 5.07 | 1 | 1 |
| 7.07 | 1 | 1 |
| 8.02 | 1 | 1 |
| 11.31 | 1 | 1 |
| 11.32 | 1 | 1 |
| 11.33 | 1 | 1 |
| 11.42 | 1 | 1 |
| 11.43 | 1 | 1 |
| 11.44 | 1 | 1 |
| 11.45 | 1 | 1 |
| 11.46 | 1 | 1 |
| 12.01 | 1 | 1 |

-continued

Test results: Water weeds
Application rate: 4 kg of active ingredient per hectare

| Comp. No. | Echinochloa | Monochoria |
|---|---|---|
| 12.14 | 1 | 1 |

What is claimed is:

1. A 1,5-substituted imidazole derivative of formula I

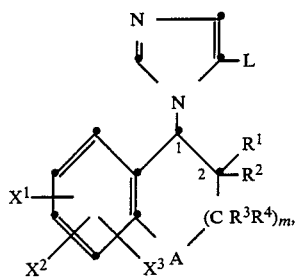
(I)

or a stereochemically isomeric form thereof, or a salt thereof, in which m is 0 or 1, A is a group

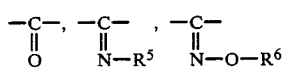

L is

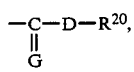

$X^1$ is hydrogen, $C_1-C_5$alkyl, $C_1-C_5$alkoxy, halogen, $C_2-C_5$alkenyl, nitro, amino, $C_1-C_5$alkylcarbonylamino, trifluoromethyl or difluoromethoxy, $X^2$ is hydrogen, $C_1-C_5$alkyl, halogen or $C_1-C_5$alkoxy, $X^3$ is hydrogen or halogen, each of $R^1$ and $R^2$, independently of the other, is hydrogen, $C_1-C_5$alkyl or $C_2-C_5$alkenyl, or $R^1$ and $R^2$ together with the carbon atom carrying them form a spirocyclic $C_3-C_7$cycloalkane ring, $R^3$ is hydrogen, $C_1-C_5$alkyl, halogen, $C_1-C_5$alkoxy or hydroxy, $R^4$ is hydrogen, $C_1-C_5$alkyl, halogen or $C_1-C_5$alkoxy, or $R^3$ and $R^4$ together with the carbon atom carrying them form a carbonyl group, or $R^2$ and $R^3$ are a $C_2-C_5$alkylene bridge; each of $R^5$ and $R^6$ is hydrogen, $C_1-C_5$alkyl, —$CH_2$—$C_2$—$C_5$alkenyl, benzyl or phenyl, each of $R^{14}$ and $R^{15}$, independently of the other, is hydrogen or $C_1-C_5$alkyl, G is oxygen or sulfur D is oxygen or sulfur and $R^{20}$ is hydrogen, $C_1-C_5$alkyl, —$CH_2$—$C_2$—$C_5$alkenyl, —$CH_2$—$C_2$—$C_6$alkynyl, $C_3-C_7$-cycloalkyl, or $C_1-C_5$alkyl substituted by $C_3-C_7$cycloalkyl, $C_3-C_7$cycloalkoxy, phenyl, $C_1-C_5$alkoxy, hydroxy, cyano,

carboxy or by $C_1-C_5$alkoxycarbonyl.

2. A compound according to claim 1, wherein $X^2$ and $X^3$ are hydrogen.

3. A compound according to claim 2, wherein $X^1$ is hydrogen, chlorine, methyl or methoxy.

4. A compound according to claim 1, wherein L is —$COOR^{20}$.

5. A compound according to claim 4, wherein L is carboxy or $C_1-C_5$alkoxycarbonyl.

6. A compound according to claim 5, wherein L is methoxycarbonyl or ethoxycarbonyl.

7. A compound according to claim 1, wherein each of $R^1$, $R^2$, $R^3$ and $R^4$, independently of the others, is hydrogen or methyl.

8. A compound according to claim 1, wherein A is the group

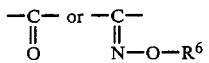

wherein $R^6$ is hydrogen, $C_1-C_5$alkyl or phenyl.

9. A compound according to claim 8, wherein A is the group

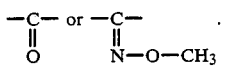

10. A compound according to claim 1, wherein $X^1$ is hydrogen, chlorine, methyl or methoxy, $X^2$ is hydrogen, methyl or methoxy, $X^3$ is hydrogen, L is a group —$COOR^{20}$, each of $R^1$, $R^2$, $R^3$ and $R^4$, independently of the others, is hydrogen or methyl and A is the group

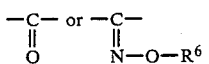

wherein $R^6$ is hydrogen, $C_1-C_5$alkyl or phenyl.

11. A compound according to claim 10, wherein L is carboxy or $C_1-C_5$alkoxycarbonyl and A is the group

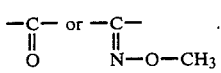

12. A compound according to claim 11, wherein L is methoxycarbonyl or ethoxycarbonyl.

13. 1-(2,2-dimethyl-3-oxoindan-1-yl)-5-imidazolecarboxylic acid methyl ester, according to claim 1.

14. 1-(2,2-dimethyl-4-oxotetralin-1-yl)-5-imidazolecarboxylic acid methyl ester, according to claim 1.

15. 1,3-trans-1-(3-bromo-2,2-dimethyl-4-oxotetralin-1-yl)-5-imidazolecarboxylic acid methyl ester, according to claim 1.

16. 1,3-cis-1-(3-bromo-2,2-dimethyl-4-oxotetralin-1-yl)-5-imidazolecarboxylic acid methyl ester, according to claim 1.

17. A herbicidal composition which, in addition to carriers and/or other adjuvants, contains as active ingredient a herbicidally effective amount of at least one 1,5-substituted imidazole derivative of formula I, according to claim 1.

18. A method of controlling weeds, which comprises treating the weeds or the locus thereof with a herbicidally effective amount of a compound of formula I, according to claim 1.

19. A method according to claim 18 for the selective control of weeds in crops of useful plants.

20. A method according to claim 19 wherein the crops of useful plants are cereals, sugar beet, rape, soybeans, maize or rice.

21. A method according to claim 19 wherein the crop of useful plants is rice.

22. A method according to claim 19 wherein the crop of useful plants is maize.

* * * * *